US009629969B2

(12) United States Patent
Salvinelli et al.

(10) Patent No.: US 9,629,969 B2
(45) Date of Patent: Apr. 25, 2017

(54) INTRANASAL ADMINISTRATION OF AGENTS WITH PRO-INFLAMMATORY ACTIVITY FOR THE THERAPY OF NEUROLOGICAL DISORDERS

(76) Inventors: Fabrizio Salvinelli, Rome (IT); Beatrice Salvinelli, Rome (IT); Emanuele Salvinelli, Rome (IT); Alessandra D'Eramo, Latina (IT)

( * ) Notice: Subject to any disclaimer, the term of this patent is extended or adjusted under 35 U.S.C. 154(b) by 390 days.

(21) Appl. No.: 14/234,360

(22) PCT Filed: Jul. 20, 2012

(86) PCT No.: PCT/IT2012/000227
§ 371 (c)(1),
(2), (4) Date: May 13, 2014

(87) PCT Pub. No.: WO2013/011536
PCT Pub. Date: Jan. 24, 2013

(65) Prior Publication Data
US 2014/0290647 A1  Oct. 2, 2014

(30) Foreign Application Priority Data

Jul. 21, 2011   (IT) .............................. RM2011A0390

(51) Int. Cl.
| | |
|---|---|
| *A61M 15/08* | (2006.01) |
| *A61K 31/4045* | (2006.01) |
| *A61K 38/08* | (2006.01) |
| *A61K 38/17* | (2006.01) |
| *A61K 31/7004* | (2006.01) |
| *A61K 33/00* | (2006.01) |
| *A61K 33/04* | (2006.01) |
| *A61K 33/14* | (2006.01) |
| *A61K 31/727* | (2006.01) |
| *A61K 38/18* | (2006.01) |
| *A61M 15/00* | (2006.01) |
| *A61K 9/00* | (2006.01) |

(52) U.S. Cl.
CPC .......... *A61M 15/08* (2013.01); *A61K 9/0043* (2013.01); *A61K 31/4045* (2013.01); *A61K 31/7004* (2013.01); *A61K 31/727* (2013.01); *A61K 33/00* (2013.01); *A61K 33/04* (2013.01); *A61K 33/14* (2013.01); *A61K 38/08* (2013.01); *A61K 38/1709* (2013.01); *A61K 38/185* (2013.01); *A61M 15/009* (2013.01)

(58) Field of Classification Search
CPC ................ A61K 33/14; A61K 2300/00; A61K 31/7004; A61K 33/00
See application file for complete search history.

(56) References Cited

U.S. PATENT DOCUMENTS

| 135,372 | A | * | 1/1873 | Schofield | ............... A61M 16/16 128/200.11 |
|---|---|---|---|---|---|
| 6,063,363 | A | | 5/2000 | Goodwin et al. | |
| 6,382,205 | B1 | * | 5/2002 | Weinstein | ........... A61M 3/0262 128/200.14 |
| 6,410,046 | B1 | * | 6/2002 | Lerner | ................. A61K 9/0009 424/400 |
| 2007/0031341 | A1 | | 2/2007 | DiMauro | |
| 2008/0014152 | A1 | | 1/2008 | Di Mauro et al. | |
| 2008/0075671 | A1 | | 3/2008 | Di Mauro | |

FOREIGN PATENT DOCUMENTS

| CA | 2 261 278 A1 | 8/2000 |
|---|---|---|
| CN | 1616087 A | 5/2005 |
| EP | 1 374 883 A1 | 1/2004 |
| FR | 2 313 914 A1 | 1/1977 |
| WO | WO 99/48361 A1 | 9/1999 |
| WO | 00/76474 A1 | 12/2000 |
| WO | WO 2007/085018 A2 | 7/2007 |

OTHER PUBLICATIONS

Baker, et al., "Acute intranasal insulin administration improves verbal memory for adults with Alzheimer's disease," Abstracts for the Annual Meeting of the Society for Neuroscience, Society for Neuroscience, Jan. 1, 2003, Washington, DC.
Craft, et al., "Intranasal Insulin Therapy for Alzheimer Disease and Amnestic Mild Cognitive Impairment: A Pilot Clinical Trial," Archives of Neurology, Sep. 12, 2011, pp. 29-38, vol. 69, No. 1.
Diener, et al., "Acute management of migraine: triptans and beyond," Medline, Jun. 1, 1999.
International Search Report, Italian Patent Application No. PCT/IT2012/000227 dated Nov. 15, 2012.
Ossipov, "Growth Factors and Neuropathic Pain," Current Pain and Headache Reports, Feb. 16, 2011, pp. 185-192, vol. 15, No. 3, Current Science Inc., New York.
Passali, et al., "Clinical evaluation of the efficacy of Salsomaggiore (Italy) thermal water in the treatment of rhinosinusal pathologies," Embase, May 1, 2008.
Silva Ram Kiran Vaka, et al., "Delivery of nerve growth factor to brain via intranasal administration and enhancement of brain uptake," Journal of Pharmaceutical Sciences, Oct. 1, 2009, pp. 3640-3646, vol. 98, No. 10.

(Continued)

*Primary Examiner* — Mina Haghighatian
(74) *Attorney, Agent, or Firm* — Arent Fox LLP

(57) ABSTRACT

The invention concerns a product consisting of distilled water or of an aqueous solution hypotonic or substantially isotonic with respect to blood plasma or, less preferably, hypertonic with respect to blood plasma, to be administered on the nasal mucosa according to a specific operation mode in order to cause an inflammation of an irritative kind, for use in a treatment of stimulation of the endogenous production of inflammatory mediators, in the therapy and prevention of neurological disorders, in particular of degenerative disorders of the central and peripheral nervous system. The inflammatory mediators the endogenous production of which is stimulated comprise NGF, neurotrophin-3, neurotrophin-4, serotonin, substance P, heparin, ECF-A.

13 Claims, 8 Drawing Sheets

(56) References Cited

OTHER PUBLICATIONS

Wilfong, et al., "The release of nerve growth factor from the nasal mucosa following toluene diisocyante," Journal of Toxicology and Environmental Health, Taylor 6 Francis, Aug. 1, 2005, pp. 1337-1348, vol. 68, No. 15, United States.
Official Communication issued in European Patent Application No. 12753843.7 dated Jul. 14, 2015.
Response to Official Communication in European Patent Application No. 12753843.7 dated Dec. 9, 2015.
Salvinelli et al., "Enhanced presence of NGF and mast cells number in nasal cavity after autologous stimulation: relation with sensorineural hearing deficit," European Review for Medical and Pharmacological Sciences, 2015; 19: 381-391.
Salvinelli et al., "High-pressure physiological saline isotonic solution administration enhances brain NGF and NGF-receptors expression," European Review for Medical and Pharmacological Sciences, 2015; 19: 3822-3832.

\* cited by examiner

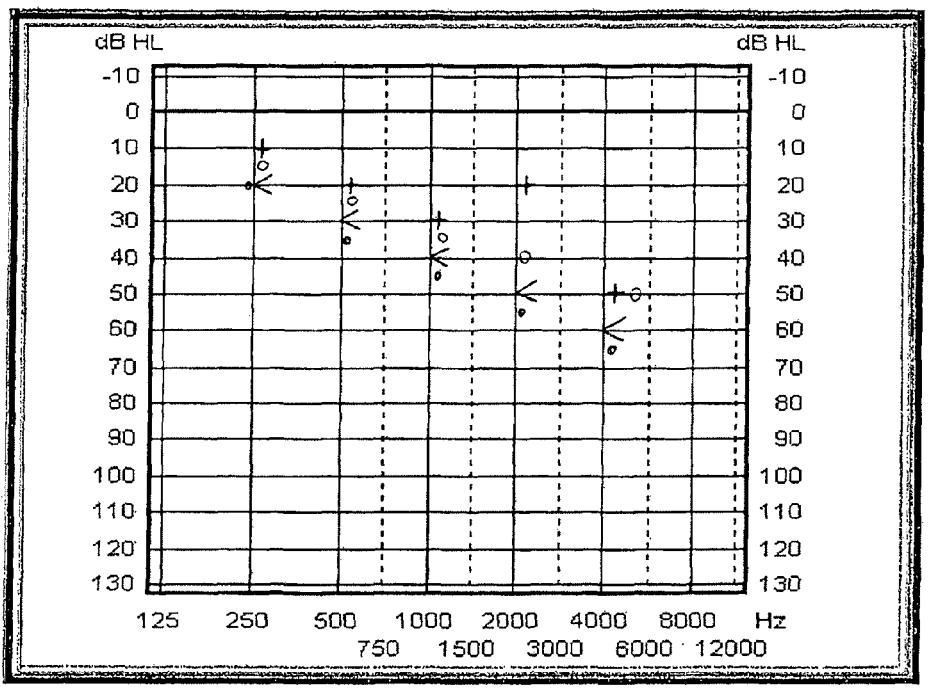
Fig 11. 160 people with sensorineural hearing loss treated for 48 months and examined with bone audiometry (BA).
< Left ear. Bone audiometry before treatment
+ Therapy: PEL 10 gr/sec, ET 10 sec, Frequency ten times a day. BA after treatment (n. 40 people)
° Therapy: PEL 0,2 gr/sec, ET 0,2 sec, Frequency once a day. BA after treatment (n. 40 people)
• Conventional therapies (n.80)

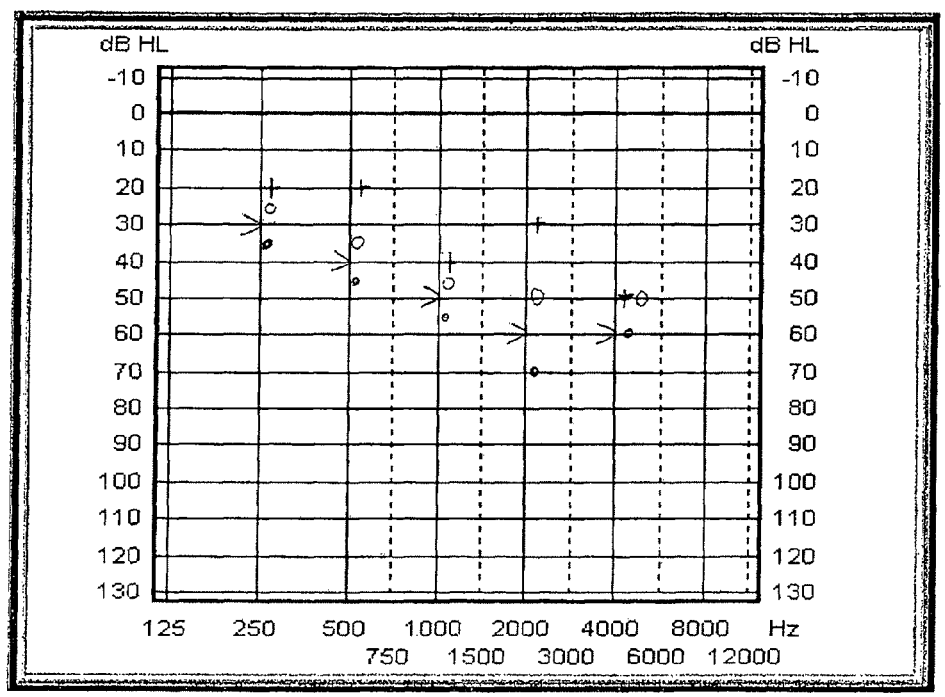
Fig 12. 160 people with sensorineural hearing loss treated for 48 months and examined with bone audiometry (BA).
< Right ear. Bone audiometry before treatment
+ Therapy: PEL 10 gr/sec, ET 10 sec, Frequency ten times a day. BA after treatment (n. 40 people)
° Therapy: PEL 0,2 gr/sec, ET 0,2 sec, Frequency once a day. BA after treatment (n. 40 people)
• Conventional therapies (n.80)

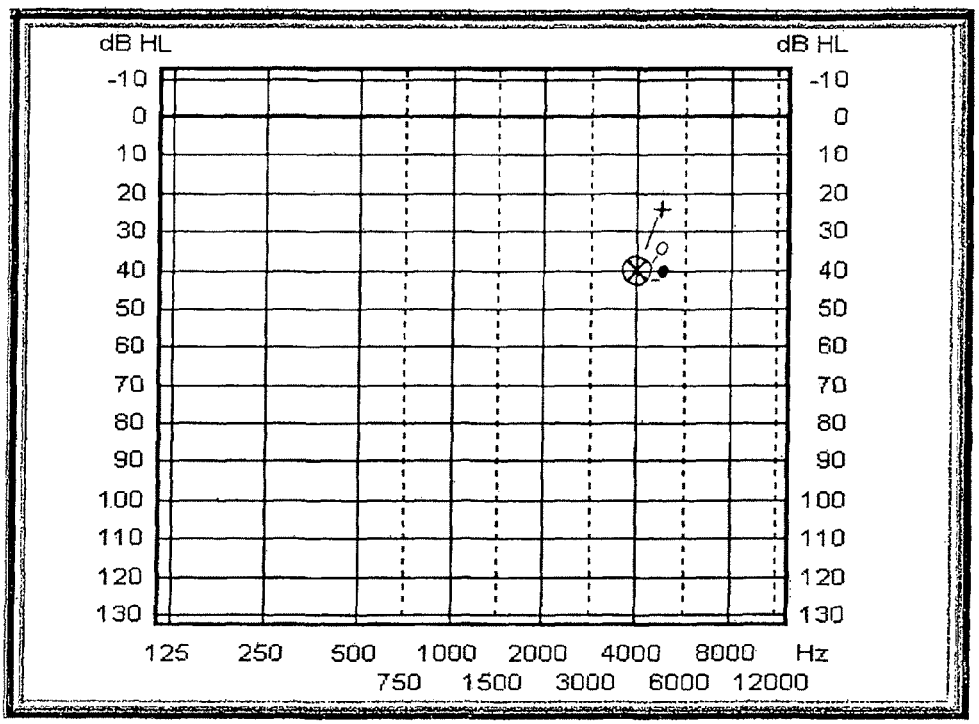

Fig.13. People (n. 216) affected by tinnitus. Measurement of tinnitus intensity, in decibel hearing level, before and after 6 months of therapy

 MEASUREMENT BEFORE THERAPY
People (n. 216) affected by tinnitus, average 40 dB intensity
MEASUREMENT AFTER THERAPY
+ People (n. 72): Therapy: PEL 7 gr/sec, ET 1 sec, Frequency ten times a day
° People (n. 72): Therapy: PEL 7 gr/sec, ET 1 sec, Frequency ten times a day
• People (n.72): Conventional therapies

INTRANASAL ADMINISTRATION OF AGENTS WITH PRO-INFLAMMATORY ACTIVITY FOR THE THERAPY OF NEUROLOGICAL DISORDERS

CROSS-REFERENCE TO RELATED APPLICATIONS

This application is a National Stage entry of International Application No. PCT/IT2012/000227, filed Jul. 20, 2012, which claims priority to Italian Patent Application No. RM2011A000390, filed Jul. 21, 2011. The disclosures of the prior applications are hereby incorporated in their entirety by reference.

FIELD OF THE INVENTION

The present invention concerns the intranasal administration of agents dispensed in such a way as to show a pro-inflammatory action, for the therapy of disorders of the nervous system. More specifically, the invention concerns a product consisting of distilled water or of an aqueous solution hypotonic or substantially isotonic with respect to blood plasma or, less preferably, hypertonic with respect to blood plasma, to be administered on the nasal mucosa according to a specific operation mode in order to cause an inflammation of an irritative kind, for use in a treatment of stimulation of the endogenous production of inflammatory mediators, in the therapy and prevention of neurological disorders, in particular of degenerative disorders of the central and peripheral nervous system. The inflammatory mediators the endogenous production of which is stimulated comprise NGF, neurotrophin-3, neurotrophin-4, serotonin, substance P, heparin, ECF-A.

BACKGROUND OF THE INVENTION

As it is known, Nerve Growth Factor (NGF) is a signaling protein involved in the development of the nervous system of vertebrates, which drives and regulates the growth and survival of neurons through cell signaling mechanisms. Such molecule is produced in many mammal tissues, including man, and is released in the bloodstream in higher amounts during the growth and differentiation of the nervous system. It is presently ascertained, actually, that NGF exerts a trophic, differentiative and tropic action on the cholinergic neurons of the central nervous system and of the peripheral nervous system, and is active more generally in the protection of the nervous system.

NGF was discovered in the 1950s by Rita Levi-Montalcini, who during thirty years continued her research on this protein molecule and the mechanism of action thereof. In 1986 she was awarded the Nobel Prize in medicine, together with the US researcher Stanley Cohen. Several studies by Montalcini and her group of researchers show that nerve cells grow when placed in contact with NGF in vitro, while the tropic action of NGF is shown by the directional growth of the nerve fibres of target cells towards an exogenous source of NGF. Thus, the production of such growth factor has the effect of causing survival of the target cells and steering the growth of their axons, so as to enhance the formation of correct synaptic contacts.

It is known that the biological effect of NGF is mediated by two receptors present on the surface of the corresponding target cells, i.e. the highaffinity TrkA (tyrosine kinase A) receptor and the low-affinity p75 receptor. The existence of many antibodies that selectively inhibit the biological effect of NGF has enabled an accurate characterisation and modulation of its activity, both in cellular systems and in vivo.

Several experimental works have shown the physiopathologic importance of NGF in preventing neuronal damage of a surgical, chemical, mechanical and ischemic origin, thus making it the ideal candidate for use not only in the prophylaxis but also in the therapy of many pathologies of the central and peripheral nervous system. For instance, NGF has been shown to be effective in the therapy of bedsores and chronic ulcers in general (Tuveri M. et al., NGF, a useful tool in the treatment of chronic vasculitic ulcers in rheumatoid arthritis, *Lancet* 2000, 356:1739-1740). In several cases patients with corneal neurotrophic ulcers, which arise in case of defective innervation, have been treated with eye-drops based on NGF obtaining a full restoration of the cornea (Bonini St. et al., Topical treatment with nerve growth factor for neurotrophic keratitis. *Ophthalmology* 2000, 107:1347-524; Lambiase A., et al., Anti-inflammatory and healing activities of nerve growth factor in immune corneal ulcers with stromal melting, *Arch. Ophthalmol.* 2000; 118:1446-9).

It has also been shown, more recently, that NGF eye-drops, upon administration on the corneal surface, can pass through the various ocular tissues, thus reaching internal structures of the eye, such as the retina and the optical nerve. Therefore, administration of NGF through the topic ophthalmic route has been proposed and successfully tested for the therapy of glaucoma as well, where such agent can perform a regeneration action on the optical nerve (Lambiase A. et al., Nerve growth factor eye drops to treat glaucoma, *Drugs News Perspect.* 2010, 23(6):361-7).

Taking into account the pathologies of the central nervous system, NGF has the property of nourishing the brain cells and preserving them from ageing and, in addition to deferring apoptosis of brain neurons, it increases their size and the important branchings connecting them with each other. This condition results in the so-called phenomenon of "neuronal plasticity".

By using the mouse animal model, it has been experimentally shown that if the animals are deprived of NGF they have memory deficits similar to the deficits caused by Alzheimer's disease. Since the main factor responsible for Alzheimer's is a peptide, i.e. beta-amyloid, the production of which in normal cells is suppressed by NGF, if NGF is removed from a culture of neural cells the production of beta-amyloid is activated in a short time. NGF has also been reported to be capable of stopping the progression of atrophy of acetylcholine-producing neurons, the reduction of which is involved in the symptomatology of Alzheimer's disease (Auld D. S. et al., Alzheimer's disease and the basal forebrain cholinergic system: relations to β-amyloid peptides, cognition, and treatment strategies, *Prog. Neurobiol.* 2002, 68:209-245; Williams B. J. et al., Nerve growth factor in treatment and pathogenesis of Alzheimer's disease, *Prog Neurobiol* 2006, 80(3):114-28).

NGF is also released in the skin, not only by neuronal fibres but also by basal keratinocytes, mast cells (or mastocytes), Merkel cells. In particular, keratinocytes, the skin cells, also express both high affinity and low affinity NGF receptors. It has been shown that NGF, more than EGF (Epidermal Growth Factor), stimulates the keratinocytes proliphuration and prevents their apoptosis. Keratinocytes exert a protective action against external agents which may be noxious on the skin, attracting the arrival of immunocytes. Therefore, it is believed that NGF may play a role also in the protection from skin disorders such as sunburn, atopic dermatitis, T cells cutaneous lymphoma, scleroderma, paraneoplastic hyperproliferative lesions, psoriasis.

It is also known that mast cells, cells involved in the immune and inflammatory response, have in their interior hundreds of granules containing various substances. When the mast cell is called upon to counter a tissue damage, for instance of allergic or inflammatory origin, or due to infection or trauma, the mast cells degranulate, releasing the substances contained therein, and in this way they protect the surrounding tissue, thus promoting the recovery thereof. NGF is among the substances released by mast cells.

From the foregoing it is apparent that, irrespective of the cellular origin thereof, an increase of NGF in a lesion site may stimulate healing also through different mechanisms than the neuronal one. Indeed, the ability shown by NGF to influence the skin cells makes it an optimal candidate to the role of modulator of the healing phases, first of all the inflammatory phase. The induction and enhancement of mast cell degranulation is believed to be the fundamental mechanism through which NGF activates the inflammatory process. The proliferative action on keratinocytes explains the role of NGF in reepithelialization, which is the key event of cutaneous healing, through which keratinocytes migrate at the lesion margins and prolipherate until they completely cover the lesion.

It has been reported in the literature that the NGF concentration is high, in combination with a great increase of mast cells, in a number of inflammatory and autoimmune conditions, including experimental allergic encephalitis (EAE), the latter representing the most widely employed model for multiple sclerosis (Calzà et al., Proliferation and phenotype regulation in the subventricular zone during experimental allergic encephalomyelitis: In vivo evidence of a role for nerve growth factor, *PNAS* 1997, 95:3209-3214). Another example is represented by the studies carried out on allergic conjunctivis, where an increase of NGF due to inflammation conditions has been reported (Bonini St. et al., Nerve growth factor: an important molecule in allergic inflammation and tissue remodeling, *Int. Arch. Allergy Immunol.* 1999, 118:159-162).

Since it has been shown that Nerve Growth Factor plays an important role in protecting the neural cells, it would be extremely useful if NGF could be administered to patients suffering from pathologies of the nerve system, both central and peripheral (CNS and PNS), or to subjects which are exposed to the risk of developing such pathologies. However, in spite of the fact that NGF has been discovered more than six decades ago, a sufficiently cheap way of producing it has not been found so far. The synthesis of human NGF through genetic engineering techniques appears to be an extremely difficult and complex task, and for this reason the murine version of NGF has been mostly employed to date, for experimental and clinical purposes. Murine NGF is extracted from rat salivary glands, and has an extremely high extraction cost as well.

In addition, in the specific case of pathologies of the CNS, such as Alzheimer's disease or Parkinson's disease, an administration of NGF by the oral or the parenteral routes is hindered by the presence of the blood-brain barrier. The latter prevents the brain tissues from being reached by concentrations of active substances sufficient to exert an appreciable therapeutic action. Actually, all of the studies carried out so far have shown an effectiveness of NGF only when it is administered by the intracerebral route (intracerebroventricularly), since this molecule is unable to pass through the blood-brain barrier in therapeutic concentrations through systemic administration.

The literature also describes attempts to stimulate the endogenous production of NGF directly in the central nervous system, with the purpose of treating neurodegenerative disorders such as Alzheimer's by administration of a suitable chemical agent, with the role of "NGF inducer". To this regard, the U.S. Pat. No. 5,281,607 (Stone et al., assigned to New York University) proposes the use of pharmacological agents, specifically α adrenergic receptor antagonists (a adrenergic antagonists or alpha-blockers) or β adrenergic receptor antagonists (beta-blockers), as agents stimulating the endogenous production of NGF. Such agents, among which the $\alpha_2$ receptor antagonists are preferred, are administered by the oral or parenteral route, although the intranasal route is mentioned among the possible routes of administration.

The U.S. Pat. No. 6,410,046 to E. Lerner (assigned to Intrabrain International) proposes a method for administering any medicament to the central nervous system through the olfactory zone, using the application of an electrical potential to obtain the transfer of the medicament through the nasal mucous membrane, in combination with the use of a permeation enhancer. The two agents, defined physical agent and chemical agent, can be applied sequentially or simultaneously to obtain the passage of the medicament to the brain through the intranasal or the transocular route. However, the introduction of an electrode in the nasal cavity and the use of an electric potential appear to be traumatic for the patient, besides being risky in view of the possible complications.

Compounds having similar pharmaceutical activity as the compounds proposed by Stone et al. are also used as "NGF inducers" in the US patent application US 2008/0014152 by M. Di Mauro et al., in particular clenbuterol, a $\beta_2$ adrenergic receptor antagonist. Di Mauro uses an intranasal administration method similar to the method proposed by Lerner, replacing the electrical means with a mechanical means, namely a spray nasal dispenser of a commercial kind with a long thin semiflexible tube connected thereto, to be placed in the nasal cavity below the cribriform plate, the thin bone layer which separates the brain from the nose. According to the document, the beta blocking agent, being sprayed through the tube oriented with its distal exit hole close to the cribriform plate, directly reaches the brain, where it exerts its action of inducing the production of endogenous NGF.

Another patent document of the same main author, the patent application US 2007/0031241 (M. Di Mauro et al.), discloses a device for easing the passage of specific medicinal substances through the cribriform plate or the meninges. The system disclosed is based, similarly to Lerner's proposal, on applying a voltage to administer therapeutical agents to the central nervous system by the intranasal route, across the cribriform plate. The administration is made by introducing a delivery device, for instance a cathodic probe, into the nasal cavity. The delivery device may have a similar shape as the devices proposed in the two previously cited documents, so as to be placed close to the cribriform plate. In this case the medicinal substances involved in the iontophoretic transfer are substances having antioxidant activity, suitable to reduce oxidative stress in the brain tissues, and not NGF inducers.

It is to be noted that the intranasal administration of pharmacologically active substances in order to obtain a bioavailability of the concerned substances in the CNS involves the actual risk of serious complications; it is dangerous since it does not take into account the fact that the cribriform plate has a distance from the nasal vestibule which varies from person to person. In addition, the bone thickness is variable, and in many cases such bone is extremely thin, so that the patient may be exposed to the risk of breaking the cribriform plate itself and to the risk of a resulting meningitis, which is a potentially lethal occurrence.

Summarizing, the prior art solutions intended to stimulate the endogenous production of NGF, or which could be used to that aim, show various drawbacks, including:

- the known difficulties due to overcoming the blood-brain barrier, it the route of administration considered is the oral or the parenteral route;
- the risk due to possible noxious effects of exogenous chemical agents, such as alfa-blockers or beta-blockers, when introduced directly in the brain tissues;
- the risk due to the use of electrical stimuli in the nose of in the brain;
- the mechanical risk due to the introduction of a delivery device, of any nature, in close proximity to the cribriform plate.

Therefore, there was a need in the prior art to find solutions which would be free from the drawbacks mentioned above.

In the frame of the research that led to the present invention, the complex series of experimental findings which led to consider nerve growth factor as a mediator of the inflammatory process. As it is known, inflammation is a response to a tissue damage having the object of insulating the zone damaged by the harmful agents and preventing the latter from diffusing into the body, and of attracting in that zone cells having anti-infective activity (leucocytes) and, finally, stimulating healing.

A fundamental role is also played by mast cells (or mastocytes), which are normally present in the connective tissue. The latter tend to concentrate particularly along the blood vessels and are now considered to be the activators of acute phlogosis. In response to an inflammatory stimulus, mast cells play a key role in starting inflammation, as they put into action substances already stored in their cytoplasmic granules, which are immediately released, and newly synthesized substances, or substances which attract (chemotaxis) white blood cells in the inflammatory zone. White blood cells play a defensive role against infection and produce themselves inflammatory mediators.

Several endogenous compounds play an ascertained role as inflammatory mediators. These include, firstly, preformed mediators, released from the mast cells secretion granules, from the secretion granules of granulocytes (which belong to the white blood cells group) and from the platelets in the extracellular environment, such as histamine and serotonin, and secondly ex novo synthesized mediators, which are synthesized in case of need, such as prostaglandins, leukotrienes, platelet activating factors (PAF), reactive oxygen species (ROS), nitrogen oxide (NO), cytokines.

The substances known as inflammatory mediators, in that they are produced by cells which take part in the inflammatory mechanism, or by cells active in attracting leukocytes (i.e. white blood cells) and mast cells in the inflammatory zone, include, as mentioned above, nerve growth factor (NGF) and the other two neurotrophins known as neurotrophin-3 (NT-3) and neurotrophin-4 (NT-4). In addition, inflammatory mediators include heparin and the other proteoglycans, serotonin, eosinophil chemotactic factor of anaphylaxis (ECF-A) and substance P.

As already noted, NGF, produced by the mast cells and released from their granules, but also produced by eosinophil granulocytes and by macrophages—all these cells taking part in the inflammatory process—is a chief molecule of a complex nerurotrophin family, which comprises neurotrophin 3 (NT-3) and neurotrophin 4 (NT-4). The latter have a protective activity on the nervous system cells which is similar to the action of NGF (Francis N. et al., NT-3, like NGF, Is Required for Survival of Sympathetic Neurons, but Not Their Precursors, *Dev. Biol.* 1999, 210: 411-423; Ulupinar E. et al., Differential Effects of NGF and NT-3 on Embryonic Trigeminal Axon Growth Patterns, *J. Comp. Neurol.* 2000, 425:201-218; Cheryl L. et al, Neurotrophin-4: A Survival Factor for Adult Sensory Neurons, *Curr. Biol.* 2002, 12:1401-1404).

Serotonin (or 5-hydroxytryptamine, 5-HT) is a neurotransmitter synthesized in the serotoninergic neurons of the CNS and in the enterochromaffin cells of the gastrointestinal tract, which is mainly involved in the regulation of mood. As noted, serotonin is considered to be a preformed inflammatory mediator, as it is present in the dense granules of platelets. The serotonin receptors are found mainly on the cell membrane of neurons in the central and peripheral nervous system, where serotonin performs its action. It plays an important role in appetite control and in the alimentary behaviour, on headache, on blood pressure, on premature ejaculation and on sleep.

Serotonin promotes the appearance of satiety feeling and in general the reduction of ingested food. For this reason some anorexia-inducing drugs, such as fenfluramine, act by increasing the serotonin signal. In addition, serotonin stimulates the reduction of carbohydrates intake due to a negative feedback. Actually, the ingestion of carbohydrates stimulates insulin production, which eases the entrance of nutrients, including amino acids and with the exception of tryptophan, in cells. Thus, the relative blood levels of tryptophan increase, this increase enhancing its entrance in the central nervous system, where it stimulates serotonin production.

Serotonin shows a euphorising and calming effect, and it is known that a correct amount of serotonin reduces stress, induces sleep and regulates the sleep cycles. It has been shown, inter alia, that the pharmacological treatment with serotonin enhances the quantity and quality of sleep. At the CNS level, serotonin is released from the presynaptic axon terminal, a part thereof acts on the postsynaptic receptor and the exceeding part is reabsorbed by the presynaptic terminal and stored in vesicles, or it is degraded by the monoamino oxidases (MAO). The MAO-inhibitor drugs act by blocking monoamino oxidases, thus bringing about in the CNS an increase of serotonin and of other brain monoamines. Well-known psychiatric medications, such as SSRIs (Selective Serotonin Reuptake Inhibitors), tricyclic antidepressants and MAO inhibitors are active on this neurotransmitter.

Some drugs with antiemetic properties are agonists of the serotonin receptors, with the aim of thus increasing its signal.

From the foregoing it is clear that a treatment capable of increasing the endogenous production of serotonin would meet a great interest in therapy.

Substance P (SP) is a short chain polypeptide that functions as a neurotransmitter and as a neuromodulator in mammals. It is produced and released by eosinophils, macrophages, endothelial cells, nerve terminals. An important role in the stimulation of SP synthesis is played by mast cells, which, upon an irritative stimulus, release endocellular inflammatory mediators and attract eosinophils and macrophages in the inflamed zone.

It is known that substance P plays an important role in pain perception and in modulation of vomiting, and is a potent vasodilator. It is also believed that the release of this neurotransmitter from the peripheral terminals of the sensory nerve fibres is involved in neurogenic inflammation, which in turn appears to be involved in the pathogenesis of headache. Actually, high concentrations of substance P prevent or reduce headache.

Another inflammatory mediator which is released by the mastocyte granules is heparin, a glycosaminoglycan having a natural anticoagulant activity. Heparin is used as a blood fluidifyer, especially in patients with a greater tendency to blood coagulation or risk factors such as atrial fibrillation, deep venous thrombosis, in subjects undergoing dialysis, to prevent the formation of thrombi and the risk of complications, also lethal, such as pulmonary thrombosis or myocardial infarction. Heparin may play a role in the prevention of clot formation in patients who underwent heart surgery or coronary stent placement.

A further inflammatory mediator of interest herein is the eosinophil chemotactic factor of anaphylaxis, ECF-A, which is mainly produced by mast cells, and has the function of attracting eosinophil granulocytes in the inflammation zone. Eosinophils represent one of the three types of granulocytes present in the blood (i.e., neutrophils, basophils and eosinophils), which are active mainly in the immune response against parasites and in allergic responses.

SUMMARY OF THE INVENTION

It has now surprisingly been found that through the stimulation of an inflammation reaction of the nasal/paranasal mucous membrane it is possible to elicit an endogenous production of NGF and other inflammatory mediators (also referred to herein as IM), in particular NT-3, NT-4, serotonin, substance P, heparin, eosinophil chemotactic factor of anaphylaxis (ECF-A). Such inflammatory mediators are thus obtained in amounts sufficient for the therapeutic treatments concerned, with no need to have recourse to expensive extractions or complex synthesis processes, but only by imitating what occurs in the normal inflammation reaction. The endogenous production of the desired IMs is triggered by administering on the mucous membranes of the nasal cavity and of the paranasal sinuses an agent which consists of distilled water or of an aqueous solution having osmolality not higher than 130% of the blood osmolality, according to specific technical features (dispensing time, amount of agent dispensed per time unit and daily frequency of the administrations) which are capable of inducing an irritation of sufficient proportions, while not being harmful, to result in an effective increase of the blood levels of the concerned IMs.

The administration features of the agents employed according to the invention, in spite of the fact that such agents are free from components with pharmacological activity, allow the appearance of an inflammation state which consequently attracts leukocytes and mast cells in the irritated tissue. The latter are, thus, stimulated directly and/or indirectly to release and produce endogenous NGF and the other inflammatory mediators in the inflamed zone, without creating the side effects typical of the introduction of other irritating substances.

The proposed administration procedure is able to stimulate the endogenous production of NGF and of the other inflammatory mediators mentioned above in the whole nasal mucous membrane, including the mucous membrane of the inferior, middle and superior turbinates, and in the whole mucous membrane of the paranasal sinuses (maxillary, ethmoid, frontal and sphenoidal sinuses). This allows, as noted before, to assure that NGF and the other IMs produced by the stimulus obtained through the concerned method reach the brain, overcoming the blood-brain barrier.

In order to exert its action, the agent according to the invention, which, as noted before, consists of distilled water or of an aqueous solution having a lower, equal or higher (by no more than 30%) osmolality than the blood plasma osmolality, must be administered according to a specific operation mode. The latter consists of dispensing time, amount of agent dispensed per time unit and daily frequency of the administrations being comprised within well-defined limits. More specifically, the effectiveness of the product is conditional upon applying the following technical features: amount of agent dispensed per second (also referred to herein by the acronym PEL, physical emission level) comprised between 0.2 g/sec and 15 g/sec, and dispensing time (also referred to herein by as ET, emission time) comprised between 0.2 seconds and 120 seconds, with the proviso that the mathematical product of ET and PEL must not go beyond 150 g of dispensed agent per each administration. Such condition is imposed by the need to make the treatment tolerable, namely not unpleasant or troublesome to the patient.

The effective daily frequency is comprised between 1 and 10 times a day, for a period of time up to the obtainment of therapeutic objects and, in any case, indefinitely in case of chronic disorders, in order to alleviate the worsening effects of the condition.

The agent according to the invention can be administered on the nasal-paranasal mucous membrane by means of spray dispensers of a commercial kind, modified in order to be able to accurately dispense the agents of the invention according to the prescribed operation mode (in particular PEL and administration time).

The agent to be dispensed according to the operation mode of the invention may consist of water, for instance distilled or deionised water, or of any aqueous solution tolerable on the nasal mucous membranes which has an osmolality comprised within the mentioned limits. Therefore, both hypotonic and isotonic (such as isotonic physiologic solution) solutions can be employed, and also, within some limits, hypertonic solutions (such as sea water), the upper limit being, as noted before, a hyperosmolality of 130% of the blood plasma osmolality. Preferably, the agent employed has an osmolality lower or equal to the blood plasma (which is 275-295 mOsm/kg on average). As such value shows some fluctuations due to age and may reach, in subjects above 78 years of age, the value of 302.2 mOsm/kg, in subjects of more than 78 years of age, the maximum upper limit of osmolality of the agent to be administered increases correspondingly.

Since the nose and the ethmoid, maxillary, sphenoidal and frontal sinuses are lined by a mucous membrane in anatomic continuity and with the same histological components, the production of endogenous NGF and of the inflammatory mediators mentioned above has been stimulated in the entire nasal mucous membrane, including the inferior, middle and superior turbinates, and in the entire mucous membrane of the maxillary, ethmoid, frontal and sphenoidal sinuses. From here, NGF and the other inflammatory mediators produced may reach the brain by exploiting 1) the diffusion to bloodstream through the lymphatic draining routes, or 2) the diffusion through the vault of the nasal cavity, the cribriform plate and the olfactory ways and then the brain, or 3) the diffusion route through the nasolacrimal duct, the nasolacrimal sac, the sclera, the optic nerve and then the brain.

BRIEF DESCRIPTION OF THE DRAWINGS

The specific features of the invention, as well as the advantages of the same and the corresponding operation modes, will be apparent with reference to the detailed description presented hereafter, and to some clinical experimental results thus obtained. The latter are illustrated by way of example in the enclosed drawings, wherein:

FIG. 11 shows the results of the left ear bone audiometry before and after the treatment in a total of 160 patients with neurosensorial hearing loss, one group of which underwent conventional therapies and the other two groups of which underwent a treatment with distilled water administered through the nasal-paranasal route according to the operating mode of the invention;

FIG. 12 shows the results of the right ear bone audiometry before and after the treatment for the same of FIG. 11; and FIG. 13 shows the results of the evaluation of tinnitus intensity, before and after a 6 months treatment, in a total of 216 patients with tinnitus, one group of which underwent conventional therapies and the other two groups of which underwent a treatment with distilled water administered through the nasal-paranasal route according to the operating mode of the invention.

DETAILED DESCRIPTION OF THE INVENTION

Figure 1:
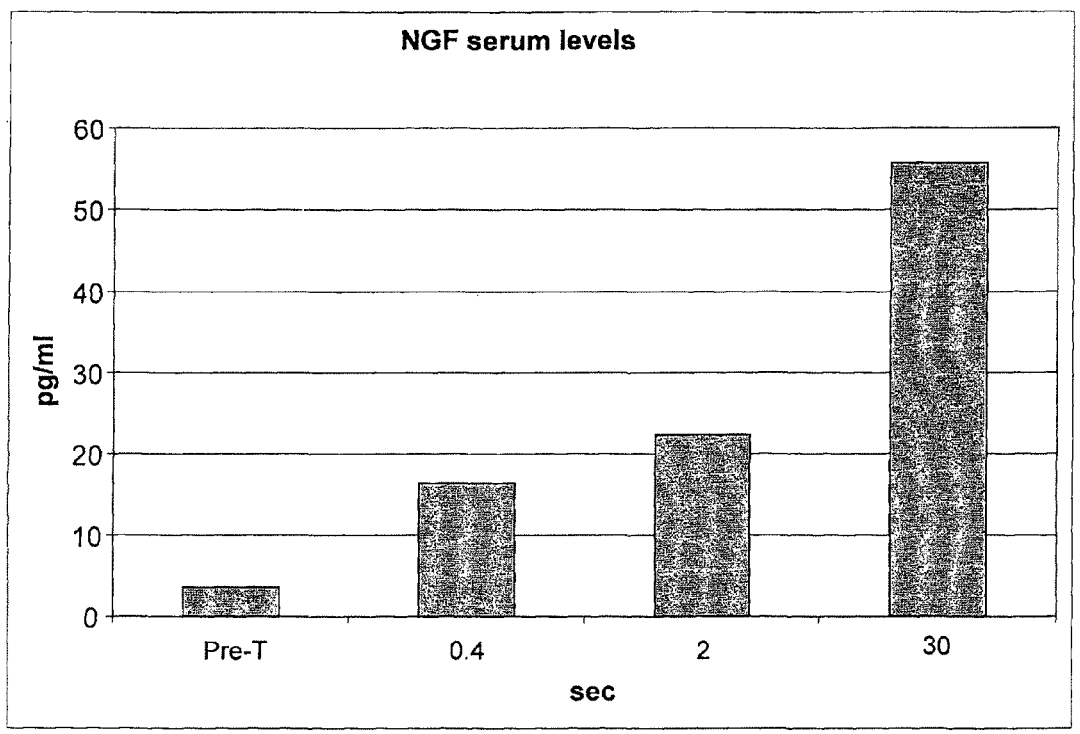
FIG. 1 shows the average NGF serum levels, pre-treatment and post-treatment, for three different groups of patients from the 236 patients who underwent a treatment with distilled water through the nasal-paranasal route according to the operating mode of the invention.
Figure 2:
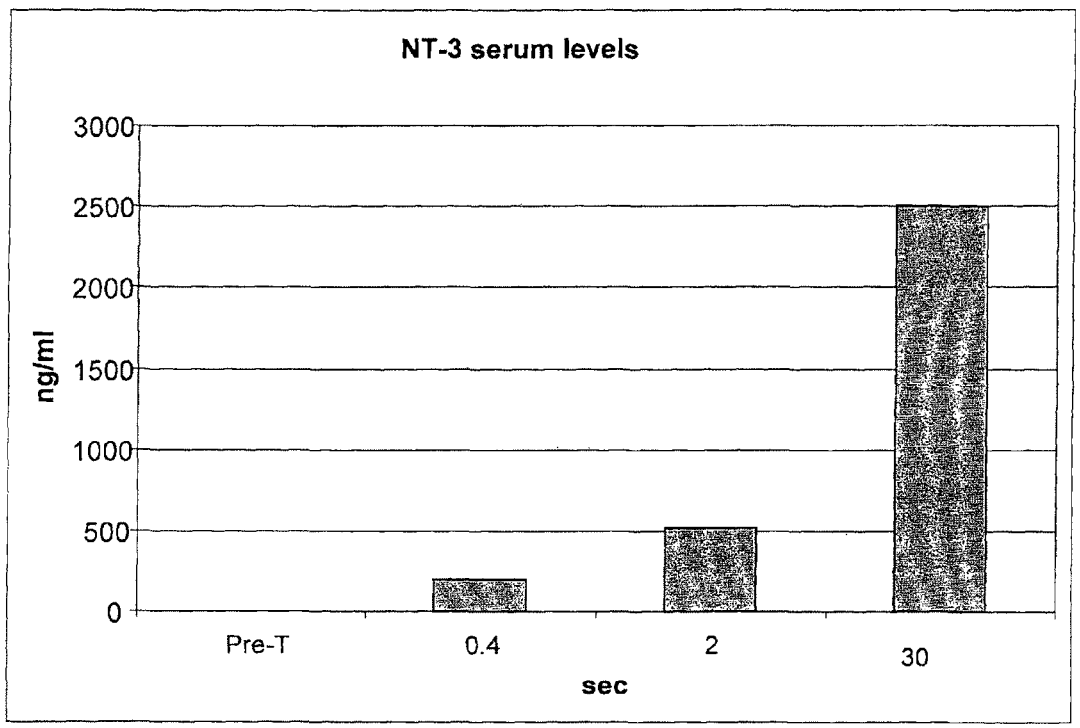
FIG. 2 shows the average NT-3 serum levels, pre-treatment and post-treatment, for three different groups of patients from the 236 patients who underwent the same treatment of FIG. 1.
Figure 3:
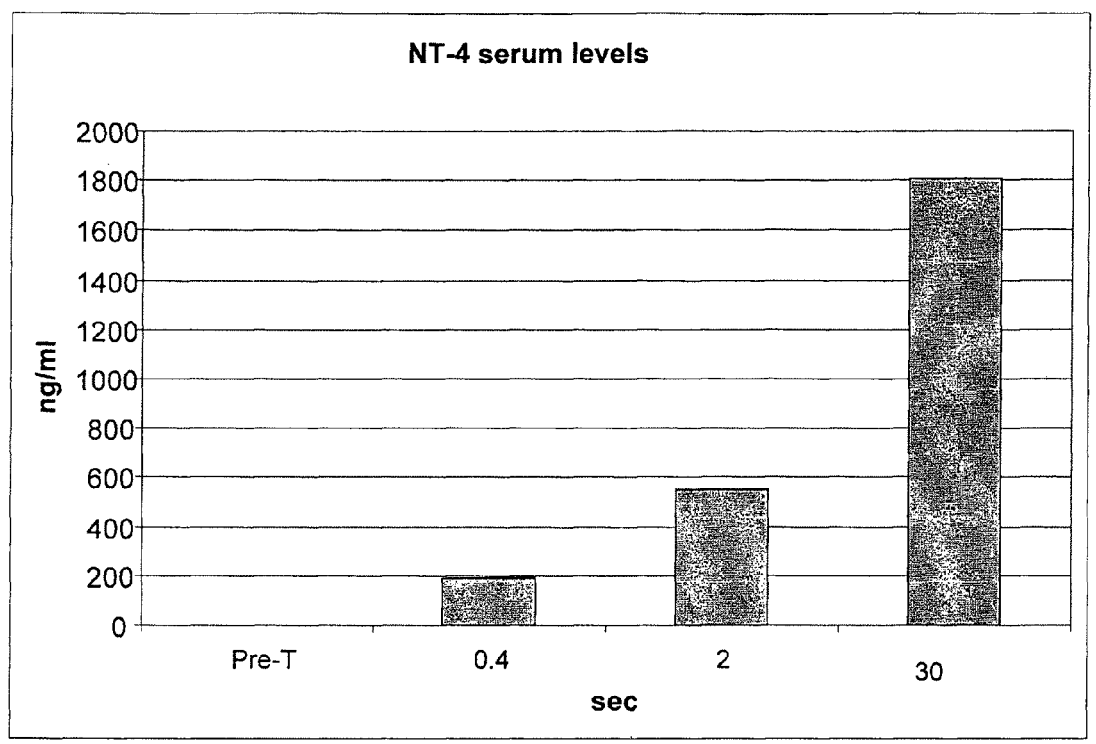
FIG. 3 shows the average NT-4 serum levels, pre-treatment and post-treatment, for three different groups of patients from the 236 patients who underwent the same treatment of FIG. 1.
Figure 4:
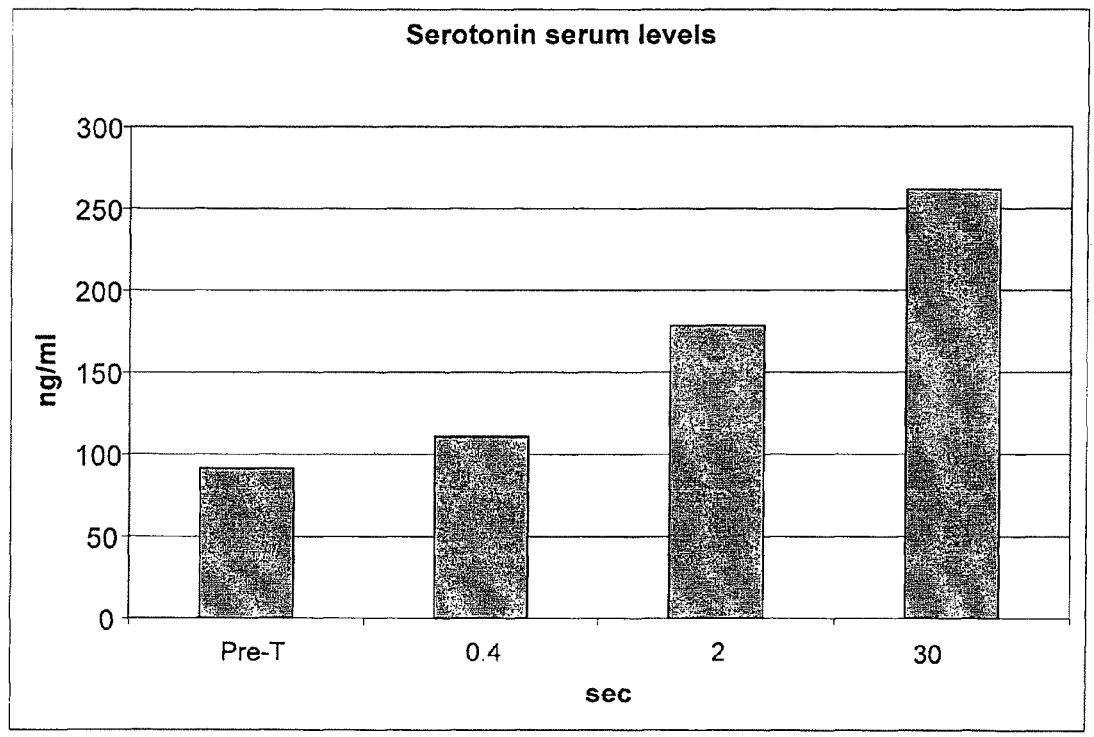
FIG. 4 shows the average serotonin serum levels, pre-treatment and post-treatment, for three different groups of patients from the 236 patients who underwent the same treatment of FIG. 1.
Figure 5:
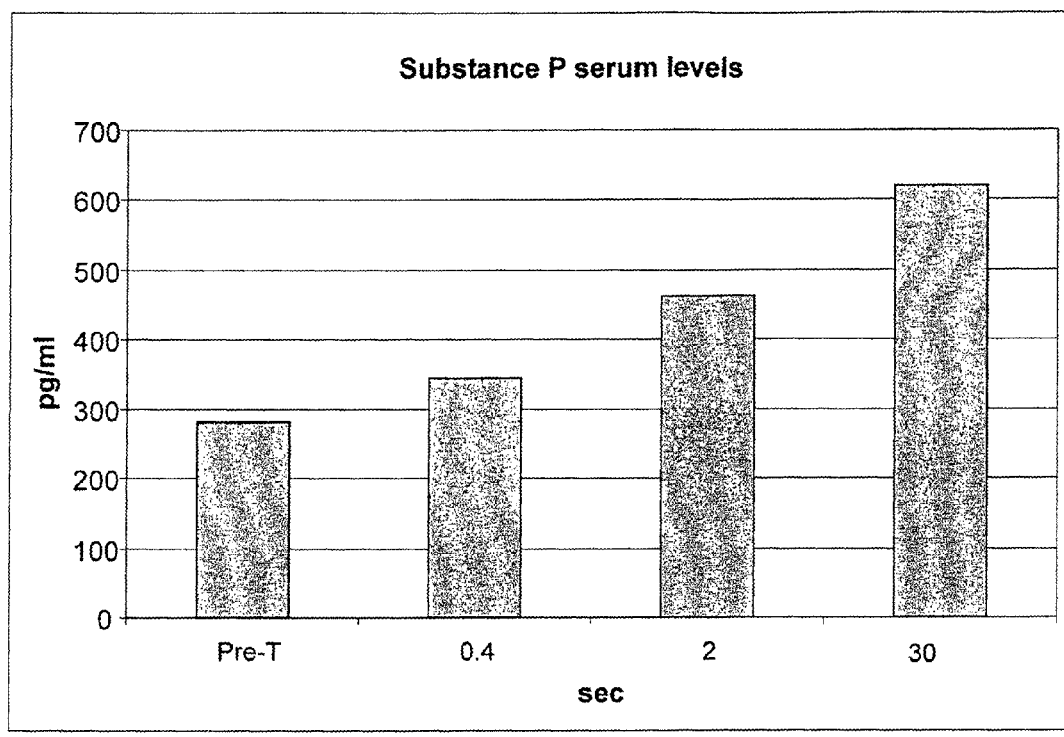
FIG. 5 shows the average serum levels of substance P, pre-treatment and post-treatment, for three different groups of patients from the 236 patients who underwent the same treatment of FIG. 1.
Figure 6:
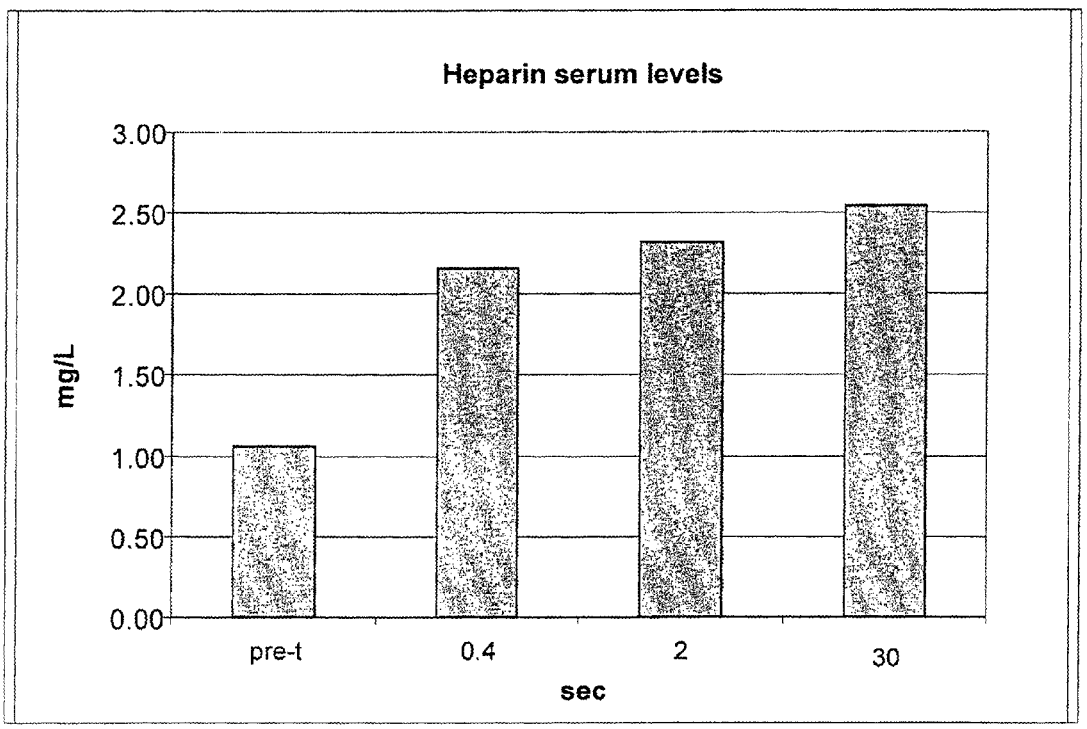
FIG. 6 shows the average heparin serum levels, pre-treatment and post-treatment, for three different groups of patients from the 236 patients who underwent the same treatment of FIG. 1.
Figure 7:
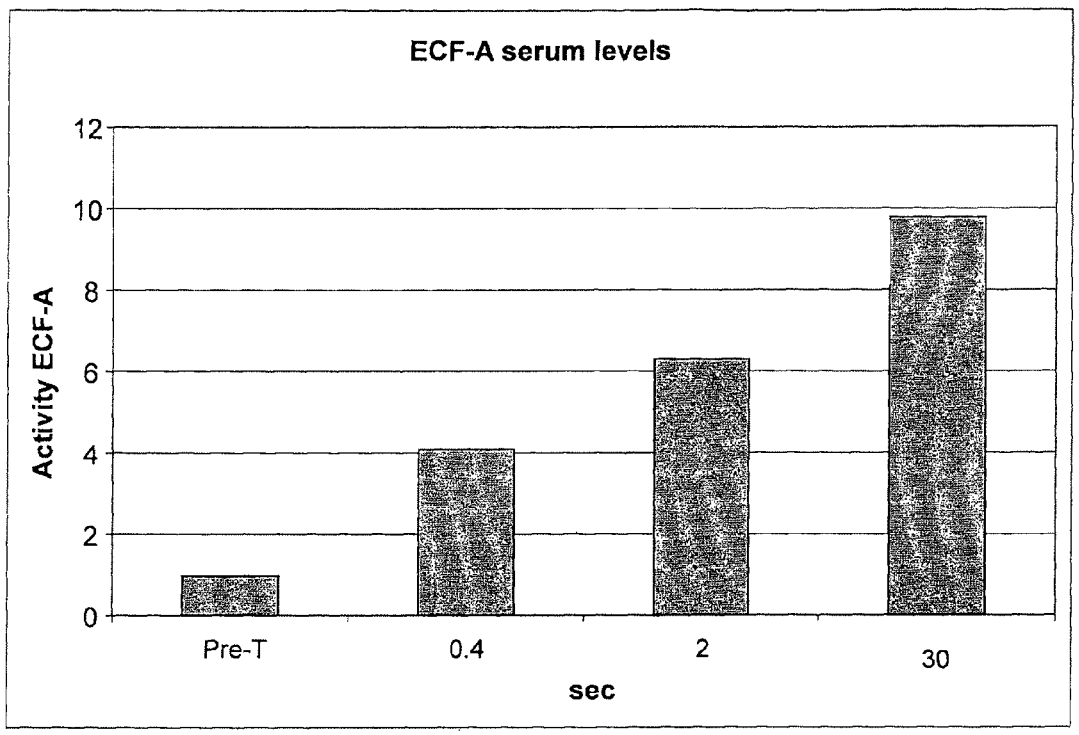
FIG. 7 shows the average serum levels of ECF-A, pre-treatment and post-treatment, for three different groups of patients from the 236 patients who underwent the same treatment of FIG. 1.

Therefore, the present invention specifically provides a product consisting of distilled water or of an aqueous solution having osmolality not higher than 130% of the blood plasma osmolality for administration on the nasal-paranasal mucous membrane, for the stimulation of the endogenous production of inflammatory mediators selected from the group consisting of NGF, neurotrophin-3, neurotrophin-4, serotonin, substance P, heparin, ECF-A, for use in the therapy and prophylaxis of pathologies of the nervous system, wherein said administration on the nasal-paranasal mucous membrane is carried out by dispensing an amount of product per second (PEL) comprised between 0.2 g/sec and 15 g/sec for a dispensing time (ET) comprised between 0.2 sec and 120 sec, with the proviso that the mathematical product of ET and PEL does not go beyond 150 g of dispensed product per each administration. According to the most general solution proposed by the invention, the administration of the product on the nasal-paranasal mucous membrane is carried out with a daily frequency comprised between 1 and 10 times a day.

According to some preferred embodiments of the invention, the administration of the product to the nasal-paranasal mucous membrane is carried out by dispensing an amount of product per second (PEL) comprised between 1.0 g/sec and 15 g/sec for a dispensing time (ET) comprised between 0.4 sec and 10 sec, with the proviso that the mathematical product of ET and PEL does not go beyond 150 g of dispensed product per each administration, while the daily frequency is still comprised between the limits mentioned above.

The simplest mode of dispensing the product according to the invention is one, or better, two sprays per nostril, followed by at least thirty deep respiratory acts, inspiratory through the nose and exspiratory through the mouth. In this way the stimulation of the mast cells resident among the epithelial cells of the nasal mucous membrane is obtained. The masts cells release inflammatory mediators and also attract other cells to release the same. Then, the deep respiratory acts stimulate the penetration of these mediators across the cribriform plate of the ethmoid, up to the cerebral liquor and in the central nervous system.

In order to make the passage of the inflammatory mediators released in the nasal-paranasal cavity through the cribriform plate up to the cerebral liquor and in the central nervous system more effective, the mode of administration of the product according to the invention can be as follows: one spray per nostril, then, after 30 minutes, another spray per nostril; closing one nostril and deep inspiration through the other nostril, and expiration through the mouth for at least thirty respiratory acts. Then a similar procedure is followed, closing the other nostril. By acting in this way, after the first spray the inflammatory cells reach the mucous membrane, through the bloodstream, in about 30 minutes. Thus, the second spray acts by stimulating not only the mast cells residing on the mucous membrane, but also the cells which reach the mucous membrane attracted by the stimulus and a greater release of inflammatory mediators is thus obtained. In the second nostril the deep respiration takes place after about 33 minutes, and a greater release of inflammatory mediators is thus obtained as well. For both administration modes the technical features reported in Table 1 hereinafter apply.

Preferably, the aqueous solution representing the product to be administered according to the invention has an osmolality lower or equal to the blood plasma osmolality, and also according to some preferred embodiments of the invention such product is chosen from the group consisting of: distilled or bidistilled water, sterile tap water, physiological solution (containing NaCl from 0.9% to 0.01% by weight, with or without the addition of glucose), Ringer solution, Ringer lactate solution, Hartmann solution, sulphur solution (in water or distilled water, with concentration from 0.1 mg to 10 mg of H$_2$S per liter), ionized alkaline water (having pH comprised between 8 and 11), deionised water and combinations thereof. More preferably, distilled water is employed as the product to be administered.

In the event that the inflammatory mediator of interest is NGF, the pathologies of the nervous system taken into account comprise disorders of the central or peripheral nervous system, neurologic pathologies of the auditory, visual or olfactory apparatus. Specifically, such pathologies may be degenerative pathologies of the central or peripheral nervous system, such as for instance Alzheimer's or presbyacusis, respectively. More specifically, said pathologies of interest are chosen from the group consisting of: Alzheimer's disease, presbiacusis, tinnitus, sudden neurosensorial hypoacusis, progressive neurosensorial hypoacusis.

In the event that the inflammatory mediator taken into account is NT-3 or NT-4, the pathologies of interest comprise pathologies of the central nervous system, pathologies of the peripheral nervous system, neurological pathologies of the auditory, visual or olfactory apparatus, degenerative pathologies of the central or peripheral nervous system.

Finally, in the event that the inflammatory mediator is serotonin, the pathologies of the nervous system of interest comprise mood disturbances, restlessness, insomnia, vegetative dystonia, depression, neurasthenia, cephalalgia, eating and appetite disorders, disorders of the quality of sleep.

According to a further aspect thereof, the present invention concerns a method for the therapy and the prophylaxis of pathologies of the nervous system by means of a stimulation of the endogenous production of inflammatory mediators selected from the group consisting of: NGF, neurotrophin-3, neurotrophin-4, serotonin, substance P, heparin, ECF-A, comprising the following steps:
  a) administering on the nasal-paranasal mucosa of a subject in need thereof a product consisting of distilled water or an aqueous solution having osmolality not higher than 130% of the blood plasma osmolality, by dispensing an amount of product per second (PEL) comprised between 0.2 g/sec and 15 g/sec for an emission time (ET) comprised between 0.2 sec and 120 sec, with the proviso that the mathematical product of ET and PEL does not go above 150 g of agent dispensed per each administration;
  b) repeating the administration as per step a) with a daily frequency comprised between 1 and 10 times a day.

According to some preferred embodiments of the invention, the operation a) is carried out by administering an amount of product per second (PEL) comprised between 1.0 g/sec and 15 g/sec for an administration time (ET) comprised between 0.4 sec and 10 sec, with the proviso that the mathematical product of ET and PEL does not go beyond 150 g of dispensed product per each administration.

Preferably, the aqueous solution employed in the method of the invention has osmolality lower than or equal to the blood plasma osmolality. According to some preferred embodiments, the product to be administered according to the invention is selected from the group consisting of: distilled or bidistilled water, sterile tap water, physiological solution (containing NaCl from 0.9% to 0.01% by weight, with or without the addition of glucose), Ringer solution, Ringer lactate solution, Hartmann solution, sulphur solution (in water or distilled water, with concentration from 0.1 mg to 10 mg of H$_2$S per liter), ionized alkaline water (having pH comprised between 8 and 11), deionised water and combinations thereof. More preferably, distilled water is employed as the product to be administered.

Clinical Experimentation

The experimentation reported herein for exemplificative purposes illustrates the results obtained with the use of the method according to the present invention.

Experiment 1

Definition of the Physical Delivery Parameters 236 informed volunteers were recruited, and they underwent blood collection before treatment for the evaluation of the blood serum concentrations of the following inflammatory mediators: endogenous NGF, neurotrophin-3, neurotrophin-4, serotonin, substance P, heparin, ECF-A (eosinophil chemotactic factor of anaphylaxis).

The volunteers were divided into 59 groups of 4 subjects each. Each group of four subjects underwent all measurements that cross an individual value of the delivery time with all the values of delivery modes (for example, 0.10 seconds of delivery for the 48 different delivery modes considered in g/sec.).

After 40 minutes from each treatment a blood sample was taken for the study of the post-treatment serum concentrations of IMs. After each blood collection, for reasons of compliance by the subjects under study, a one week break was set. Owing to the various hindrances that have occurred to the individual participants the overall study lasted two years. 236 subjects underwent each of the 48 evaluations. 11,328 measurements have thus been carried out.

All subjects were treated with nasal-paranasal spray delivery of distilled water. For the administration of the irritant agent of the present invention dispensers similar to those already on the market were used, suitably adapted to be able to deliver the product of the invention according to the required delivery mode and physical features. The physical features of each delivery were from 0.1 g/sec to 15 g/sec of PEL, with delivery times from 0.1 seconds to 121 seconds, and a frequency of once a day for 10 days, according to the following tables.

(table follows)

| GROUP 1 VALUES—PEL (physical emission level), g/sec 48 groups with PEL from 0.10 g/sec to 15.00 g/sec ||||||
| --- | --- | --- | --- | --- | --- |
| 0.10 | 0.11 | 0.12 | 0.13 | 0.14 | 0.15 |
| 0.16 | 0.17 | 0.18 | 0.19 | 0.20 | 0.30 |
| 0.40 | 0.50 | 0.60 | 0.70 | 0.80 | 0.90 |
| 1.00 | 2.00 | 3.00 | 4.00 | 5.00 | 6.00 |
| 7.00 | 8.00 | 9.00 | 10.00 | 11.00 | 12.00 |
| 12.20 | 12.30 | 12.40 | 12.50 | 12.60 | 12.70 |
| 12.80 | 12.90 | 13.00 | 14.00 | 14.20 | 14.40 |
| 14.50 | 14.60 | 14.70 | 14.80 | 14.90 | 15.00 |

| GROUP 2 VALUES -ET (emission time), sec 59 groups with ET from 0.1 sec. to 121 sec. ||||||||||
| --- | --- | --- | --- | --- | --- | --- | --- | --- | --- |
| 0.10 | 0.11 | 0.12 | 0.13 | 0.14 | 0.15 | 0.16 | 0.17 | 0.18 | 0.19 |
| 0.20 | 0.21 | 0.22 | 0.23 | 0.24 | 0.25 | 0.26 | 0.27 | 0.28 | 0.29 |
| 0.30 | 0.40 | 0.50 | 0.60 | 0.70 | 0.80 | 0.90 | 1.00 | 2.00 | 3.00 |
| 4.00 | 5.00 | 6.00 | 7.00 | 8.00 | 9.00 | 10.00 | 11.00 | 12.00 | 13.00 |

-continued

| GROUP 2 VALUES -ET (emission time), sec 59 groups with ET from 0.1 sec. to 121 sec. | | | | | | | | | |
|---|---|---|---|---|---|---|---|---|---|
| 14.00 | 15.00 | 16.00 | 17.00 | 18.00 | 19.00 | 20.00 | 21.00 | 22.00 | 23.00 |
| 25.00 | 30.00 | 50.00 | 100.00 | 110.00 | 115.00 | 119.00 | 120.00 | 121.00 | |

It should be noted that for the highest amounts of dispensed product per time unit (PEL), combined with the longest dispensing times (ET) (and therefore for the highest total amounts of agent dispensed per administration) it has not been possible to run tests due to refusal by the subjects. This allowed defining, as described in the following, the tolerance limits within which the experiments reported have been carried out. The maximum accepted time (ET) averaged 120 seconds per administration, the maximum accepted frequency averaged 10 times, the delivery flow rate (amount of agent delivered per second) was up to 15 g/sec on average, but the product of the values of ET and PEL was tolerable only so long as it did not exceed 150 g per delivery.

Results

The data reported below detected in the course of the trials are representative of the effectiveness of the treatment of the invention to stimulate the endogenous production of the inflammatory mediators taken into account. Table 1 below shows the serum pre-treatment and post-treatment mean levels of each of the seven IMs being studied, for three groups of 4 subjects each, among those who participated in the trial described herein, treated once daily for 10 days. Each of the three groups received the treatment according to the invention with a different couple of values of the ET and PEL parameters, among those indicated in the two preceding tables.

TABLE 1

Pre-and post-treatment IM serum levels for three groups of 4 subjects each, with different values of the physical delivery parameters

| | | PEL 5 g/sec | | |
|---|---|---|---|---|
| IM | | ET 0.4 sec | ET 2 sec | ET 30 sec |
| NGF | pre | | 3.7 ± 1.5 pg/ml | |
| | post | 16.3 | 22.3 | 55.8 |
| NT-3 | pre | | 0.8 ± 0.4 ng/ml | |
| | post | 203 | 516 | 2498 |
| NT-4 | pre | | 0.5 ± 0.3 ng/ml | |
| | post | 190 | 550 | 1812 |
| Serotonin | pre | | 91 ± 23 ng/ml | |
| | post | 111 | 179 | 262 |
| Substance P | pre | | 282 ± (110) pg/ml | |
| | post | 346 | 462 | 620 |
| Heparin | pre | | 1.65 mg/Litre | |
| | post | 2.16 | 2.32 | 2.54 |
| ECF-A[1] | pre | 1 (reference value for activity) | | |
| | post | 4.1 | 6.3 | 9.8 |

[1]For ECF-A quantification, the activity is defined as the number of eosinophils completely migrating through a 5 fields' random filter at 450x magnification (using vit. B 12 and phenol red as molecular markers).

The data shown in Table 1 are also illustrated in histogram form, separately for each inflammatory mediator considered, in FIGS. 1-7 of the accompanying drawings, as previously mentioned. In all seven diagrams attached, a significant increase of post-treatment serum levels may be noted, for each one of the seven IMs under study.

From the data analysis, it resulted that for PEL (amount of dispensed product per second) values between 0.1 g/sec and 0.19 g/sec, changes in serum levels of IM obtained for any ET value were not significant. The minimum effective threshold PEL is therefore 0.2 g/sec.

Similarly, as regards the dispensing time, from the same data it was found that for dispensing times from 0.1 sec to 0.19 sec, the modified serum levels of IMs obtained for any value of PEL were not significant, and therefore, the minimum effective threshold of ET is 0.2 sec.

From the data analysis it was also observed that for ET 0.2 sec significant increases were obtained with PEL 5 g/sec ($p<0.05$), in a trend of greater significance that reached for PEL at 7 g/sec a value $p<0.01$, while for PEL at 15 g/sec $p<0.001$ (discomfort felt by 100% of the subjects, who reported that they would not have borne a higher value).

Furthermore, it was found the maximum value for PEL in g/sec tolerated by ET of 0.2 sec or higher (threshold 15 g/sec) but with discomfort reported by subjects, who claimed that they would not undergo a higher value.

Accordingly, using values of PEL equal to 0.2 g/sec or more the maximum amount of ET used has been 120 sec. average, with 100% of subjects accusing discomfort, and values $p<0.001$. The PEL value of 15 g/sec and ET value of 120 sec were the maximum tolerable by the subjects, which reported that they would not undergo treatments with higher values, thereby defining the maximum parameters threshold for the treatment according to the invention that must not be exceeded, either for PEL or ET.

The maximum value of the total amount of agent delivered allowed to be tolerable has also been found, as already mentioned, for each application, being equal to 150 gr. Therefore, the values of ET and the PEL must be harmonized to avoid exceeding this limit. Furthermore, the study has allowed evidencing the existence of a value of direct proportionality between the values of ET and PEL and the production of the inflammatory mediators (IMs) considered.

Therefore, based on the foregoing, the following technical features were determined:

Technical feature 1—excellent effectiveness and tolerability of distilled water.

Technical feature 2—effective value of PEL and of ET for each delivery: PEL from 0.2 g/sec to 15 g/sec, ET from 0.2 sec to 120 sec.

Technical feature 3—minimum effective threshold (minimum effective stimulation level, MESL): ineffective below PEL 0.2 g/sec. and ET 0.2 sec.

Technical feature 4—maximum discomfort threshold (discomfort level, DL): treatment refused by subjects for PEL values above 15 g/sec and for ET values below 120 sec.

Technical feature 5—direct proportionality between the values of PEL and ET and release of IMs.

In order to realize a treatment which is well tolerated by patients, using the most effective but tolerable values of PEL and ET, especially in view of the fact that many of the nervous and degenerative diseases require a chronic therapy, further studies have been carried out, which led to determine the following additional characteristics.

Technical feature 6—the most effective parameters tolerated by the subjects under examination are PEL 2.0 g/sec to 15 g/sec, together with ET between 2.0 sec. and 75 sec., with a limit of maximum delivery for each single administration of 150 g and a frequency from 1 to 6 times daily. Also in this case the maximum delivery value does not refer to the effectiveness, rather to the tolerability, as above this parameter the therapy is not well tolerated.

Technical feature 7—relationship between PEL and ET: it is possible to increase a parameter and decrease to the other proportionally, while remaining above the minimum effective threshold (MESL), in order to achieve similar increasing results in the IMs. The increase of PEL is more important than the increase of ET, based on the same substance dispensed for each administration.

Experiment 2

Aqueous Solutions Different from Distilled Water

Further tests were carried out on a group of 220 people. All subjects were submitted to blood sampling before treatment, for the evaluation of blood serum concentrations of the following inflammatory mediators: NGF, neurotrophin-3, neurotrophin-4, serotonin, substance P, heparin, ECF-A.

The subjects were treated by delivering, by the nose-paranasal route according to the invention, one of the following liquids:

distilled or bidistilled water, sterile water, saline solution (containing NaCl from 0.9% to 0.01% weight, specifically 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%. 0.01%, with or without addition of glucose), Ringer solution, Ringer lactate solution, Hartmann solution, sulphur solution (in water o distilled water, concentration 0.1 mg to 10 mg of $H_2S$ per liter, specifically 10.0 mg/L, 9.0 mg/L, 8.0 mg/L, 7.0 mg/L, 6.0 mg/L, 5.0 mg/L, 4.0 mg/L, 3.0 mg/L, 2.0 mg/L, 1.0 mg/L, 0.9 mg/L, 0.8 mg/L, 0.7 mg/L, 0.6 mg/L, 0.5 mg/L, 0.4 mg/L, 0.3 mg/L, 0.2 mg/L, 0.1 mg/L), sea water (in which the average concentration of dissolved salts ranges from 25 to 50 g per liter, composed in majority of sodium chloride, in presence of nitrates, phosphates, oxygen and carbon dioxide, specifically 50.0 g/L, 49.0 g/L, 48.0 g/L, 47.0 g/L, 46.0 g/L, 45.0 g/L, 44.0 g/L, 43.0 g/L, 42.0 g/L, 41.0 g/L, 40.0 g/L, 39.0 g/L, 38.0 g/L, 37.0 g/L, 36.0 g/L, 35.0 g/L, 34.0 g/L, 33.0 g/L, 32.0 g/L, 31.0 g/L, 30.0 g/L, 29.0 g/L, 28.0 g/L, 27.0 g/L, 26.0 g/L, 25.0 g/L), Ionized alkaline water (pH comprised between 8 and 11), deionised water.

All subjects were treated with nasal-paranasal delivery of the test substances using PEL 5.0 g/sec to 0.4 sec and ET with a frequency of once per day, for a treatment period of 10 days. The PEL and ET parameters were selected because they were, among those in Experiment 1 with distilled water, both well tolerated and showing significant post-treatment increases compared to pre-treatment, with $p<0.01$.

All subjects underwent blood sampling 4 hours after treatment. The resulting IM values have been examined; these results were all increased in post-treatment serum, and a statistical analysis was carried out with respect to pre-treatment values, comparing the IM increases in post-treatment blood serum with the one obtained with distilled water that had been already examined statistically ($p<0.01$).

For all of the liquids tested, the results of blood serum increments of IMs obtained after the treatment were statistically significant, with p-value of at least less than or equal to 0.05, with the exception of sea water (in which the average concentration of salts dissolved ranged from 25 to 50 g/L), for which the values of the increases were not statistically significant. In summary, serum increasing values of IM post-treatment with substances under examination compared to distilled water in terms of values of statistical significance were:

equal: for deionised water and for sulphur solution with distilled water and $H_2S$ 0.1 mg/L lower: for water, saline, Ringer; Ringer lactate, Hartmann solution, sulphur solution (with drinking sterile water and all concentrations of $H_2S$ in trial, or with distilled water and $H_2S$ 10 mg/L), Ionized alkaline water, not significant: for sea water (wherein the average concentration of dissolved salts ranged from 25 to 50 g/L).

The experiments described above have shown that the irritative stimulus obtained by administration of an agent consisting mainly of water according to the methods of the present invention is effective for all inflammatory mediators, but this effect was not statistically demonstrated in the case of sea water.

For further confirmation a variation in the experiment has been introduced, selectively studying the concentration of NT-3 in nasal secretions prior to treatment and forty minutes after the treatment itself, which was carried out using all the liquids in question including the distilled water, with PEL of 7.0 g/sec and ET of 0.4 sec. The average value of NT-3 prior to treatment was 0.1 pg/ml, and after the treatment it was 70+50 pg/mL, with $p<0.001$. Significant differences were not detected with distilled water.

Therefore, it was confirmed that the inflammatory mediators (IM) were released in the nose-paranasal mucosal in equal proportion with all the aqueous liquid tested for the treatment, but then they were not found in similar proportions in the blood.

After an analysis of analogies between the various water-based liquids used for experimentation in comparison with the respective effects of the treatment in terms of blood levels of the Ns considered after the treatment, it was found that the detectable differences in behaviour were tied to the osmolality of each of the different aqueous liquids under test.

In practice, between the different tested liquids,
those with osmolality below blood plasma osmolality, such as distilled and deionised water, exhibited the same behaviour in terms of statistical significance of the IM increases determined with their application ($p<0.01$);

all of the isoosmolal liquids, such as sterile tap water, physiological saline (NaCl 0.9% by weight), Ringer solution, Ringer lactate solution, Hartmann solution, ionized alkaline water, etc. stimulated the IMs increase to a lesser extent compared to distilled water but still in a statistically efficient way ($p<0.03$, o $p<0.05$);

sea water, hyperosmolal compared to blood plasma and compared to distilled water, does not give increments of the IM values post-treatment that are statistically significant, in none of the concentrations examined.

On the basis of the foregoing, it was therefore established, in frame of the research that led to the present invention, that the aqueous solutions used for the nose-paranasal stimulus have a greater efficacy the lower is their osmolality. The increase values in IM production are not statistically significant for high hyperosmolality solutions, they are significant starting from values of mild hyperosmolality, and they are very significant ($p<0.05$) for isoosmolal solutions and are extremely significant ($p<0.01$) for greatly hypoosmolal liquids.

Technical feature 8—maximum effectiveness of deionised water, similar to distilled water; good effectiveness of water, saline, Ringer solution; Ringer lactate solution, Hartmann solution, ionized alkaline water, sulphur solution. Inverse proportionality between the osmolality of the liquid delivered and the production and presence of IM substances in the blood (and the effectiveness of the therapy).

To further validate the technical feature 8 the same solutions were used that gave results of significant serum increase of IMs compared to pre-treatment values—distilled water and bidistilled water, deionised water, Ringer, Ringer lactate, Hartmann solution, alkaline ionized water—making them hyperosmolal with the addition of 5 g/L of NaCl each.

20 subjects were recruited for the experiment, they underwent blood sampling before and 4 hours after treatment. The latter was performed in the same way: PEL of 5.0 g/sec and ET of 0.4 sec, once per day for 10 days. In confirmation of the technical feature 8, after the treatment increase values of IMs were found in the blood serum, which are not significant compared to the pre-treatment values.

Experiment 3

Study on the Frequency of Delivery and Duration of Treatment 60 informed volunteers were recruited, and they underwent blood collection before treatment for the evaluation of the serum concentrations of the following inflammatory mediators: NGF endogenous, neurotrophin-3, neurotrophin-4, serotonin, substance P, heparin, ECF-A.

The sixty volunteers were all subjected to the treatment according to the invention, by administration of distilled water with PEL 5.0 g/sec and ET of 0.4 sec, once a day for one day. Then, maintaining the same physical parameters of delivery the frequency of daily treatments has been increased. Blood was collected and the serum concentrations were evaluated after 40 minutes from the end of administration of each agent.

By way of example, taking into account that the behaviour of other IMs is substantially comparable, the results of dosages of only NT-3 are reported in Table 2 below.

TABLE 2

Serum levels of NT-3 pre- and post-treatment with PEL 5.0 g/sec and ET 0.4 sec average values for a group of 60 subjects.

| Pre-treatment (ng/ml) | 0.7 | | | | |
|---|---|---|---|---|---|
| Daily frequency | 1 | 2 | 3 | 4 | 34 |
| Post-treatment (ng/ml) | 0.8 | 1.1 | 2.1 | 9.1 | 202.2 |

The serum values of NT-3 obtained after treatment showed a trend of increase directly proportional to the increase of daily frequency of treatments, up to the maximum frequency of 34 times per day. From a comparison of these results with those obtained in the Experiment 1, where for the same parameters of PEL 5.0 g/sec and ET 0.4 sec, once daily for 10 days values of NT-3 equal to 203 ng/mL were obtained, the technical feature 9 was defined, as follows.

Technical feature 9—the duration of therapy in days is more important than the daily frequency of treatment: in fact, one administration per day for 10 days for a total of 10 administrations, achieves the same result of 34 administrations in a single day.

To check the effect of the total number of days of treatment, the same 60 subjects, whose IM pre-treatment values had already been measured, were all subjected to the treatment according to the invention for the intranasal and paranasal delivery of distilled water with PEL of 5.0 g/sec and ET 0.4 sec, once daily for 60 days. After 40 minutes from the end of each day of treatment, the subjects underwent blood sampling and serum dosage of the IMs above.

In the following Table 3 the average percent of increases (Δ%) of the serum values of NGF detected after each day (G) of therapy are shown for the sake of brevity, taking into account that the behaviour of other IMs resulted to be similar. The pre-treatment value of NGF was 3.6 pg/mL.

TABLE 3

Increases in average serum levels during treatment with NGF PEL 5.0 g/sec and ET 0.4 sec - average values for a group of 60 subjects

| G | Δ % | G | Δ % | G | Δ % | G | Δ % | G | Δ % | G | Δ % |
|---|---|---|---|---|---|---|---|---|---|---|---|
| 1 | +2.7 | 11 | +361.1 | 21 | +462.2 | 31 | +499.7 | 41 | +499.8 | 51 | +496.7 |
| 2 | +4.5 | 12 | +368.9 | 22 | +474.4 | 32 | +498.5 | 42 | +498.2 | 52 | +498.7 |
| 3 | +8.7 | 13 | +372.1 | 23 | +470.4 | 33 | +496.5 | 43 | +496.9 | 53 | +491.7 |
| 4 | +30.5 | 14 | +389.2 | 24 | +465.3 | 34 | +495.2 | 44 | +499.8 | 54 | +492.2 |
| 5 | +69.3 | 15 | +401.9 | 25 | +497.1 | 35 | +491.5 | 45 | +497.8 | 55 | +490.1 |
| 6 | +108.2 | 16 | +411.2 | 26 | +490.5 | 36 | +493.2 | 46 | +497.6 | 56 | +486.9 |
| 7 | +181.7 | 17 | +415.6 | 27 | +488.7 | 37 | +491.1 | 47 | +497.5 | 57 | +486.1 |
| 8 | +261.2 | 18 | +427.1 | 28 | +500.7 | 38 | +490.2 | 48 | +494.8 | 58 | +490.1 |
| 9 | +302.1 | 19 | +431.1 | 29 | +501.7 | 39 | +489.2 | 49 | +499.5 | 59 | +486.1 |
| 10 | +352.7 | 20 | +458.3 | 30 | +502.2 | 40 | +495.2 | 50 | +495.1 | 60 | +486.7 |

Figure 8:
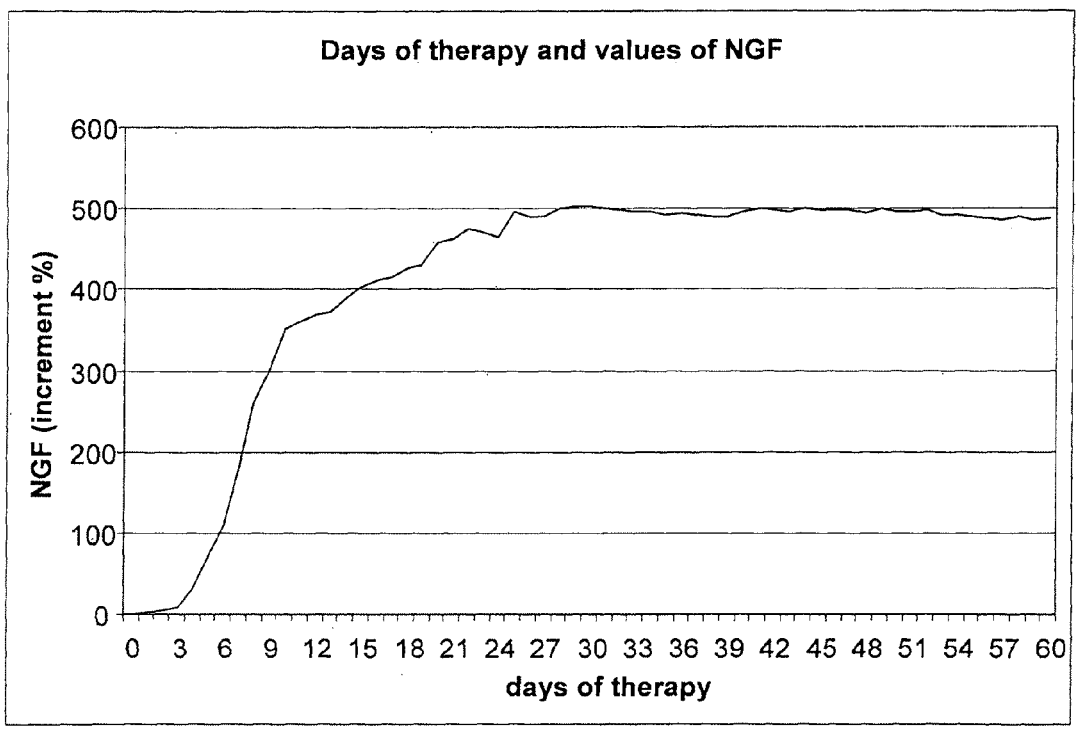
FIG. 8 shows the time course (days of therapy) of the NGF blood serum level of 60 subjects who underwent a treatment with distilled water through the nasal-paranasal route according to the operating mode of the invention.

From the above data, which are also illustrated in the form of diagram, in FIG. 8 of the accompanying drawings, it is noted that with the treatment proposed according to the invention a progressive increase in serum levels of NGF during the first days of therapy is obtained, with a maximum rate of increase on G10 and a slower but steady growth until G30. Subsequently, there d was a substantial steady state of the levels reached on G30, which did not increase any more for the rest of the treatment.

A similar trend, as noted, is obtained for blood serum levels of all the other IMs examined: NT-3, NT-4, serotonin, substance P, heparin, ECF-A.

From the foregoing, the following feature results.

Technical feature 10—with increasing days of treatment, a progressive increase of the IM blood serum levels is achieved in the first days of therapy, with a maximum rate of increase up to day 10 of therapy, and with slower but steady growth until day 30, after which a substantially steady state is reached.

It is clear that in the degenerative diseases of the nervous system, which in most cases are chronic diseases, the longest duration of therapy provides the best protective effect. The product of the invention can be administered, in case of degenerative diseases, for the whole duration of patient's life, as besides being effective it is also devoid of side effects.

From a comparison of the data of this experiment with Experiment 1 it results that, for example, for NGF in Experiment 1 with a single supply of distilled water at PEL 5 g/sec and ET 2500 sec. an increase in the NGF blood value was found, in 10 days, from the initial value of 3.7 pg/mL to 61.3 pg/ml, equivalent to 1556%. This increase is well above the increase obtained with lower values of the parameters PEL and ET, after 30 or 60 days. (see FIG. 8).

From the foregoing, therefore, the technical feature 11 results.

Technical feature 11—the increase in PEL parameters, once the minimum threshold of efficacy (MESL) is overcome, is more effective than an increase in days of therapy. It causes, in fact, an increased production of IMs which is higher, in proportion, than the increase caused by an increase of the duration of the therapy.

Furthermore, the observation of the results summarised in the technical feature 10 shows that after 30 days of therapy a steady state is reached in the production of NGF, NT-3, NT-4 and all other IMs considered. Thus a therapeutic effect is achieved as long as the therapy, which is well tolerated, is continued. Hence the following technical feature 12.

Technical feature 12—in chronic diseases of the nervous system, the therapy has the best protective efficacy if maintained over time in the course of the disease.

Table 4 below summarizes the technical features of the method of treatment according to the invention as defined above.

TABLE 4

Technical features of the treatment to stimulate the endogenous production of IMs by nose-paranasal administration of water or aqueous solutions with specific physical parameters 1. excellent effectiveness and tolerability of distilled water;
2. effective value of PEL and of ET for each delivery: PEL from 0.2 g/sec to 15 g/sec, ET from 0.2 sec to 120 sec;
3. minimum effective threshold (minimum effective stimulation level, MESL): ineffective below PEL 0.2 g/sec. and ET 0.2 sec;
4. maximum discomfort threshold (discomfort level, DL): treatment refused by subjects for PEL values above 15 g/sec and for ET values below 120 sec;
5. direct proportionality between the values of PEL and ET and release of IMs;
6. the most effective parameters tolerated by the subjects under examination are PEL 2.0 g/sec to 15 g/sec, together with ET between 2.0 sec. and 75 sec., with a limit of maximum delivery for each single administration of 150 g and a frequency from 1 to 6 times daily;
7. relationship between PEL and ET: it is possible to increase a parameter and decrease the other proportionally, while remaining above the minimum effective threshold (MESL), in order to achieve similar increasing results in the IMs. The increase of PEL is more important than the increase of ET, based on the same substance dispensed for each administration;
8. maximum effectiveness of deionised water, similar to distilled water; good effectiveness of water, saline, Ringer solution; Ringer lactate solution, Hartmann solution, ionized alkaline water, sulphur solution. Inverse proportionality between the osmolality of the liquid delivered and the production and presence of IM substances in the blood (and the effectiveness of the therapy);

TABLE 4-continued

Technical features of the treatment to stimulate the endogenous production of IMs by nose-paranasal administration of water or aqueous solutions with specific physical parameters 9. the duration of therapy in days is more important than the daily frequency of treatment: in fact, one administration per day for 10 days for a total of 10 administrations, achieves the same result of 34 administrations in a single day;
10. with increasing days of treatment, a progressive increase of the IM blood serum levels is achieved in the first days of therapy, with a maximum rate of increase up to day 10 of therapy, and with slower but steady growth until day 30, after which a substantially steady state is reached;
11. the increase in PEL parameters, once the minimum threshold of efficacy (MESL) is overcome, is more effective than an increase in days of therapy;
12. in chronic diseases of the nervous system, the therapy has the best protective efficacy if maintained over time in the course of the disease.

Experiment 4

Check on the Animal Model

To confirm the efficiency of the administration, 28 rabbits aged 1 month, of the same strain, were used. A group of 14 rabbits, named group 1, was sacrificed and the brain concentration of NGF at the protein level was studied by ELISA.

The other group, named Group 2, was divided into two sub-groups: 7 rabbits in group 2a and 7 rabbits in group 2b. The rabbits of the group 2a were treated with distilled water by intranasal spray delivery for 10 consecutive times in 12 hours, with a value of PEL 0.2 g/sec to 0.2 sec; the rabbits of the group 2b were treated with delivery of intranasal spray of distilled water 10 times a day, with a PEL value 10 g/sec for 10 sec.

All rabbits of Group 2 were sacrificed after 40 minutes after the last administration. Brain values of NGF in the encephalon nave been studied by ELISA, and these values were compared with the pre-treatment values. The presence of NGF with the average values reported in the following Table 5 has been found.

TABLE 5

Average values of NGF in the brain without treatment (group 1) and with treatment with two regimes of PEL and ET different (groups 2a and 2b)

|  | Group 1 (pg/mg) | Group 2a (pg/mg) | Group 2b (pg/mg) |
| --- | --- | --- | --- |
| Olfactory bulb | 4 | 12 | 16 |
| Hippocampus | 4 | 5 | 7 |
| Amygdala | 3.5 | 4.7 | 6 |

The increases in the concentration of NGF after treatment resulted to be statistically significant compared to the untreated group 1, both in group 2a ($p<0.005$) and in group 2b ($p<0.001$—p values of the $\chi^2$ test).

Also serotonin concentration was assessed in the brain stem of the untreated rabbits of Group 1. This resulted to be equal on average to 0.09 micrograms/mg protein in the extracellular fluid, while in the corresponding rabbits sacrificed after treatment the serotonin concentration was found to be 1 pg/mg. The difference was statistically significant ($p<0.001$—p values of the $\chi^2$ test).

The foregoing confirms that another inflammatory mediator results to be in increased concentration in the brain stem after the treatment according to the invention.

Experiment 5

Effectiveness for Mental Acuity

The product according to the invention was tested on 60 volunteers who were recruited with the payment of a fee. They were treated by administration of distilled water 1 or 10 times a day for six months, to check the results on their intellectual efficiency. The volunteers, aged between nineteen and fifty-five, all with high school degree, were randomized into two groups labelled 1 and 2, of 30 people. The subjects of group 1 were treated with administration of distilled water once per day by intranasal spray, with PEL 0.2 g/sec for 0.2 sec, and the subjects of group 2 were treated with a administration of distilled water 10 times a day, by intranasal spray with PEL of 10 g/sec for 10 sec.

All volunteers underwent blood sampling for studying the following inflammatory mediators: NGF, neurotrophin-3 and neurotrophin-4, serotonin, substance P, heparin, ECF-A before treatment and at the end of treatment.

To 15 subjects of group 1 and 15 of group 2 a test of mental acuity A was proposed and six months later a test of similar complexity B was proposed. In contrast, to 15 subjects of group 1 and 15 subjects of group 2 a test of mental acuity B was proposed, and after six months a test of comparable complexity A, always at ten o'clock of Sunday morning. The test had thirty questions with four multiple choice, to each of which the volunteers had to reply within 30 seconds.

Before treatment, there were 499 correct answers from group 1 and 491 correct answers from group 2, while at the end of treatment, the global average was 554 correct answers from group 1 and 602 correct answers from group 2. Statistical analysis showed p values of $\chi^2$ tests significant for an improvement of mental acuity in group 1 with p<0.05 and in group 2 with p<0.001. The increase in post-therapy values of NGF and its protective action of nerve cells appeared also statistically significant in Group 1 while it still gave best results with the stimulation at greater frequency and amounts of administered agent.

The values of the inflammatory mediators detected in blood before and after the end of treatment resulted to be in both groups, in the global comparison and for each subject, higher at the end of the treatment than at the beginning, as is shown in Table 6 below.

TABLE 6

Increases in serum levels of IMs after treatment for 2 groups of 30 subjects each, with different values of the physical parameters of administration

| IM | Group 1 PEL 0.2 g/sec ET 0.2 sec Freq. 1 die | | Group 2 PEL 10 g/sec ET 10 sec Freq. 10 die | |
|---|---|---|---|---|
| | Δ % | test $\chi^2$ | Δ % | test $\chi^2$ |
| NGF | +138 | p < 0.005 | +642 | p < 0.0001 |
| NT-3 | +1210 | p < 0.0001 | +123.650 | p < 0.00001 |
| NT-4 | +1144 | p < 0.0001 | +176.900 | p < 0.00001 |
| Serotonin | +40 | p < 0.05 | +235 | p < 0.05 |
| Substance P | +42 | p < 0.05 | +234 | p < 0.05 |
| Heparin | +38 | p < 0.05 | +42 | p < 0.05 |
| ECF-A | +112 | p < 0.005 | +608 | p < 0.0001 |

As it can be seen from the data above, the increase in post-treatment compared to pre-treatment was statistically significant in all cases, although for different values of p.

In group 2, which received the treatment with the most energetic parameters and with a daily frequency of 10 administration per day, increments of NT-4 and NT-3 in serum are reported, respectively going from 0.5 ng/ml to 885 ng/ml and from 0.8 ng/ml to 990 ng/ml.

The presented experiments confirm that the factors of inflammation are actually produced locally by the nasoparanasal mucosa due to stimulation of that tissue, and then from there they reach the bloodstream through the lymphatic drainage pathways to the circulatory system. To confirm this, in fact, an increase of the concentration of inflammatory mediators is found in the blood which is statistically significant already with the stimulus at a lower frequency and smaller amount of delivery, and becomes even more significant with the stimulus of higher frequency and greater amount of delivery, for further evidence of the effectiveness of the proposed treatment of the invention.

Experiment 6

Effectiveness in Patients with Alzheimer's Disease 20 patients with Alzheimer's disease in a moderate to mild stage were treated, the stage being confirmed by the Mini Mental State Examination (MMSE) (Folstein M F et al., Mini-mental state". A practical method for grading the cognitive state of Patients for the clinician, 1975, *Journal of psychiatric research* 12 (3):189-98).

The test consists of thirty questions, which refer to seven different cognitive areas: orientation in time, spatial orientation, word registration, attention and calculation, recall, language, constructive praxis. The total score ranges from a minimum of 0 to a maximum of 30 points. A score less than or equal to 18 indicates severe impairment of cognitive ability, a score between 18 and 24 indicates a moderate to mild impairment, a score of 25 is considered the limit, from 26 to 30 indicates normal cognition.

All 20 patients were subjected to the MMSE before treatment, reporting scores between 18 and 24. The patients were then treated for twelve consecutive months with the treatment according to the invention, by applying 2 sprays per nostril once a day with a PEL 5 g/sec and 0.4 sec ET.

Figure 9:
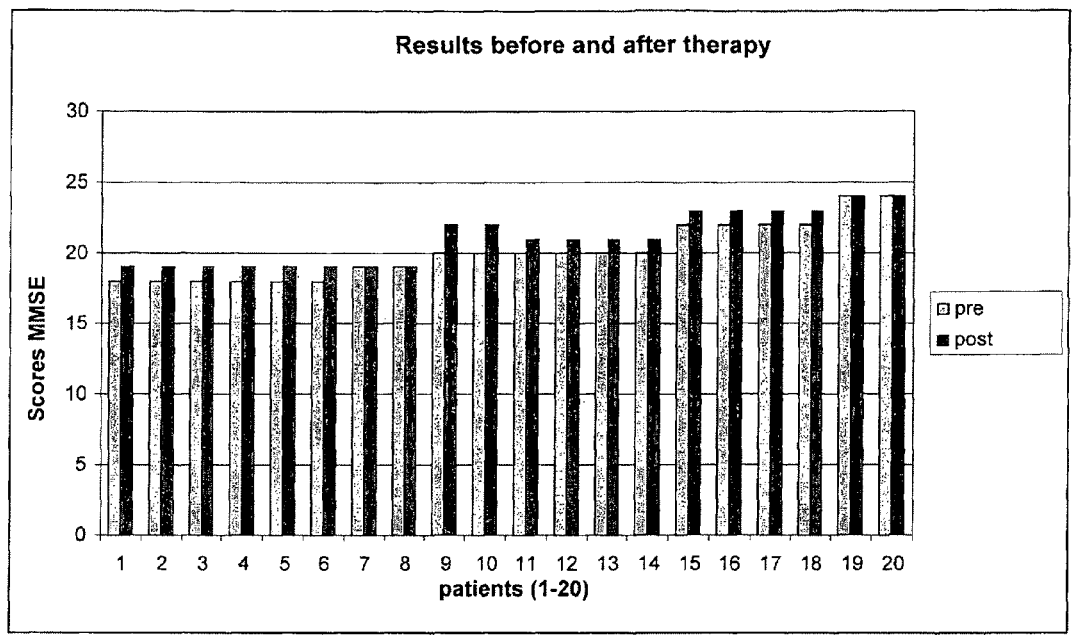
FIG. 9 shows the results, before and after therapy, of the Mini Mental State Examination scores in each of 20 patients with Alzheimer's disease who underwent a treatment with distilled water administered through the nasal-paranasal route according to the operating mode of the invention.

At the end of treatment the MMSE was performed again and the values of each patient were compared. As shown in the histogram of FIG. 9 of the accompanying drawings, all patients presented an improvement in the score of the MMSE, which is increased in all but four, in which remained unchanged while it is known that the course of Alzheimer is gradually worsening.

Figure 10:
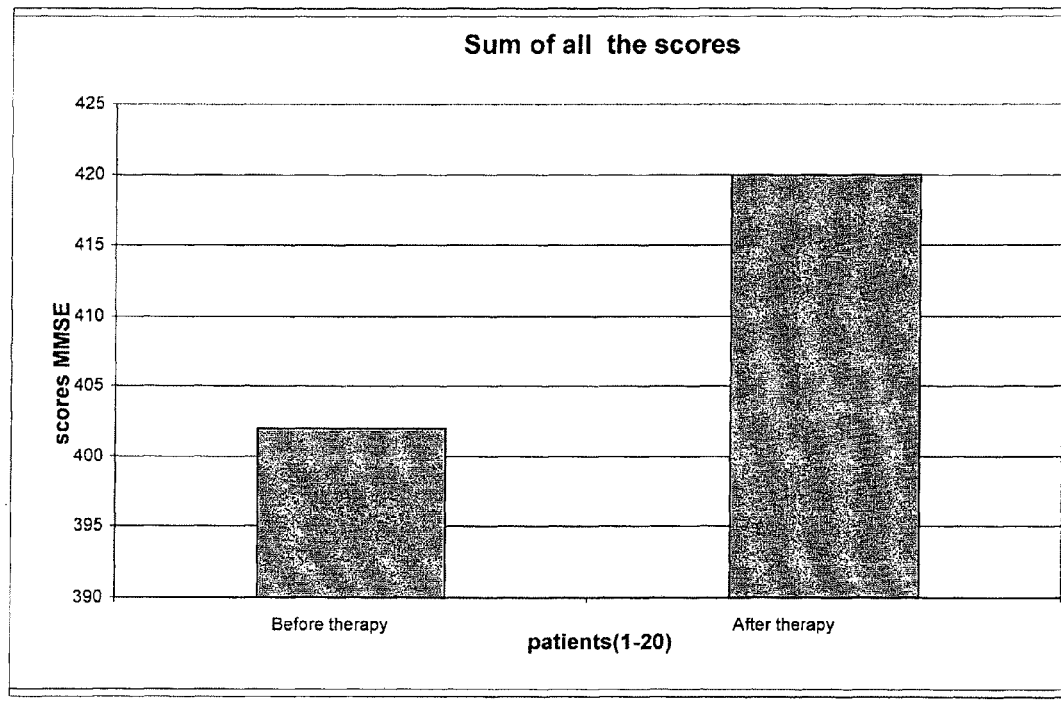
FIG. 10 shows the results of the clinical test of FIG. 9 in terms of the sum of the scores of all patients, respectively before and after therapy.

In order to evidence the effectiveness of the treatment according to the invention, in the attached FIG. 10 the results of the same experiment, in histogram form, are shown as the sum of the scores of all twenty patients before treatment (402), in comparison with the sum of the scores of all patients after treatment (420).

The values of the inflammatory mediators detected in the blood of twenty subjects before and after treatment, in the global comparison and for each subject, were higher after treatment than at the beginning, for all seven inflammatory mediators considered here. In particular, by comparing the concentrations of NGF, NT-3 and NT-4 detected in the blood before therapy and immediately after the last administration, a statistically significant increase was found in post-treatment compared to pre-treatment values for both NT-3 and NT-4 (p<0.00001) and for NGF (p<0.0001) (p values of the $\chi^2$ test).

The improvement of the symptoms of Alzheimer's disease after therapy was then correlated to the increase in the blood of neurotrophins NGF, NT-3 and NT-4 obtained with the therapy.

Experiment 7

Activity on Patients Affected by Neurosensorial Hearing Loss

Were also treated patients suffering from bilateral neurosensorial hearing loss (BNHL), which consists of a lowering of hearing caused by irreversible suffering of the inner ear hearing cells. This condition is considered incurable by medical science today, with positive and progressively worsening.

A total of 160 patients (volunteers and informed), 80 males and 80 females, with BNHL with average hearing thresholds between 50 and 80 dB for frequencies from 125 Hz to 8000 Hz, ranging in age from 18 to 75 were randomized in two groups of 80 subjects, referred to as group 1 and group 2. Group 1 was divided into two subgroups of 40 subjects each, called 1a and 1b. The first group was treated with administration of intranasal spray of distilled water once per day, with a PEL 0.2 g/sec for an ET of 0.2 sec., while group 1b was treated with administration of intranasal spray of distilled water 10 times a day, with a PEL of 10 g/sec for 10 sec. Both groups were treated on a daily basis for 48 months.

The subjects of group 2, used as control, were treated with common commercial drugs for this kind of pathology (vasoactive drugs and multivitamin complexes having specific action on the inner ear).

After forty-eight months of treatment revealed an improvement of the hearing threshold in group 1, treated with the method according to the invention by an average of 5 dB per ear in group 1a, and 10 dB in group 1b, while in group 2 it was found a worsening in the average of 5 dB for ear, with a statistically significant difference in favour of the first treatment (p<0.001) for both the first and for the group 1b.

Moreover, comparing the group's first audiogram pre- and post-treatment has identified that statistically significant improvements are obtained either for the group 1a (p<0.005) or for group 1b (p<0.001), while group 2 presented a worsening post-treatment statistically significant (p<0.005).

The overall results of the clinical tests described are illustrated by diagrams in FIGS. 11 and 12 of the accompanying drawings, which show, respectively as follows:

FIG. 11: Left Ear
  < Results of bone audiometry (AO) pre-treatment (160 subjects)+
  + Group 1B, (40 subjects)—therapy PEL 10 g/sec, ET 10 sec, frequency 10 times/day: AO post-treatment
  ○ Group 1A, (40 subjects)—therapy PEL 0.2 g/sec, ET 0.2 sec, frequency 1 time/day—AO post-treatment
  • Group 2, (80 subjects)—traditional therapies
FIG. 12: Right Ear
  < Results of bone audiometry (AO) pre-treatment (160 subjects)+
  + Group 1B, (40 subjects)—therapy PEL 10 g/sec, ET 10 sec, frequency 10 times/day: AO post treatment
  ○ Group 1A, (40 subjects)—therapy PEL 0.2 g/sec, ET 0.2 sec, frequency 1 time/day—AO post treatment
  • Group 2, (80 subjects)—traditional therapies Both figures show an improvement in the hearing threshold after 48 months of treatment: the first group by an average of 5 dB per ear, and in group 1b of 10 dB, while in group 2 it is noticed a decline in average of 5 dB per ear.

In all subjects included in the experiment the blood concentration of inflammatory mediators has been detected in the same way than in experiment 5 (tests of mental acuity). The values of the inflammatory mediators detected in the blood before treatment and at the end of the same, in global comparison for each subject, were all, in both the groups, higher at the end of the treatment than at the beginning, as is shown in Table 7

TABLE 7

Increases in serum levels of IMs post-treatment for 2 groups of 40 subjects each, treated with different values of the physical delivery parameters

| | Group 1a PEL 0.2 g/sec ET 0.2 sec Freq. 1 per die | | Group 1b PEL 10 g/sec ET 10 sec Freq. 10 per die | |
|---|---|---|---|---|
| IM | Δ % | test $\chi^2$ | Δ % | test $\chi^2$ |
| NGF | +120 | p < 0.005 | +669 | p < 0.0001 |
| NT-3 | +1010 | p < 0.0001 | +131.328 | p < 0.00001 |
| NT-4 | +1244 | p < 0.0001 | +214.900 | p < 0.00001 |
| Serotonin | +44 | p < 0.05 | +219 | p < 0.05 |
| Substance P | +45 | p < 0.05 | +239 | p < 0.05 |
| Heparin | +42 | p < 0.05 | +44 | p < 0.05 |
| ECF-A | +115 | p < 0.005 | +582 | p < 0.0001 |

As it can be seen from the data above, the increase post-treatment compared to pre-treatment was statistically significant in all cases, although for different values of p.

In group 1b, which received the treatment with the most energetical parameters and with a frequency of 10 administrations per day, increments of NT-4 and NT-3 in serum are reported, ranging respectively from 0.4 ng/ml to 860 ng/ml and 0.7 ng/ml to 920 ng/ml.

In group 2, not treated with the method of the present invention, no significant difference between the serum concentrations of IMs before and after the treatment was detected.

Also in this test the protective action either of NGF or of NT-3 and NT-4 of nerve cells appeared significant also statistically. The results were even better with the stimulus with greater frequency and greater quantity of delivery.

In addition, the experiment confirms what is evident in test 1: factors of inflammation, locally produced by the nose-paranasal mucosa due to stimulation of that tissue, then from here reach the blood circulation via the respiratory lymphatic drainage toward the circulatory system. The production of inflammatory mediators has a statistically significant increase even with the stimulus at a lower frequency and smaller amount of delivery, but even better results are obtained with stimulation at higher frequency and increased quantity of delivery.

Experiment 8

Effectiveness on Increase of Serotonin Levels and Other Assessments on Patients Recruited in Experiment 7

To evaluate the effect of increased production and release of serotonin, has been given another questionnaire to 40 participating subjects of group 1a of Experiment 7, with the following questions, to be completed before and after treatment:

1) Define the level of hunger before and during treatment, in a scale of from 0 to 10, where 0=no hunger and 10=big hunger.

Results: average pre-treatment=6, average during treatment=4.5. The reduction of the hunger level post-treatment compared to the values of pre-treatment appears to be statistically significant (p<0.05—values of p in the test $\chi^2$).

2) Define the level of mood before and during treatment in a scale of from 0 to 10, wherein 0=very bad mood and 10=exceptional good mood. Results: average pre-treatment=5, average post-treatment=7. The increase in good mood post-treatment compared to pre-treatment was statistically significant (p<0.05—values of p in the test $\chi^2$).

3) Define the quality of sleep before and during the treatment in a scale of from 0 to 10, wherein 0=sleeping very bad and 10=very good sleeping.

Results: average pre-treatment 5, average post-treatment 7. The improvement during treatment compared to pre-treatment was statistically significant (p<0.05—values of p in the test $\chi^2$).

4) To 20 male patients, aged between 20 and 65 years, sexually active, the following question was asked: Define the quality and duration of sexual act with the same partner in the previous year and during the treatment, in a scale of from 0 to 10, wherein 0=sexual act of no personal satisfaction and 10=sexual act of an exceptional level of satisfaction.

Results: pre-treatment average 5, post-treatment average 8. The improvement during treatment compared to pre-treatment was statistically significant (p<0.001—values of p in the $\chi^2$ test).

To evaluate the effect of increased production and release of substance P, the subjects were asked to measure the arterial pressure, or have been advised parents to register their children in case of minors, first and during therapy, again at ten o'clock in the morning.

Results: pre-treatment average 140/80 (average recorded in the previous week), while during the treatment was 120/65 (average recorded throughout the period of therapy). The reduction in blood pressure during treatment compared to pre-treatment values was statistically significant (p<0.05—values of p in the $\chi^2$ test).

To evaluate the effect of the production and release of the ECF-A the entities in question have responded to the following question: Define for frequency and severity of infectious episodes in the pre-treatment period and during the treatment period, scaling from 0 to 10, where 0=very bad situation, and 10=exceptional situation.

Results: pre-treatment average 5.5, post-treatment average 7.5.

The reduction in frequency and severity of infectious episodes during the treatment compared to pre-treatment was statistically significant (p<0.05—values of p in the test $\chi^2$).

Experiment 9

Evaluation of the Efficacy on Tinnitus

In another experiment 250 subjects suffering from tinnitus for at least thirty days were selected. Tinnitus was perceived in the right ear or left or indefinitely in the head.

Tinnitus is an auditory sensation that does not correspond to an acoustic stimulus, due to the suffering of the internal ear cells for inflammatory trauma, infection, chronic and/or acute exposure to loud noise or from vascular disease and many other causes. The more Tinnitus is perceived as strong, the more it is annoying for the person affected. This is a disorder of the nervous tissue that does not respond to current therapies, so that once started, it often remains present throughout life, often increasing its degree of intensity and discomfort for the patient.

All patients, informed and recruited in the experiment with the payment of a fee, were visited, by a paid otolaryngologist, to exclude extraneous causes for the suffering of the hair cells. Patients with dermatitis or external ear infections, ear infections with acute or chronic otitis, with tympanic perforation, with middle ear diseases such as otosclerosis were thus excluded. 216 subjects were been selected in this way, all of which have performed a hearing test and a measurement of the intensity of tinnitus: acufenometria, to define the frequency in Hertz (Hz) and the intensity in decibels (dB) of the tinnitus.

The patients were divided into three groups: Group A, Group B, Group C, each of 72 subjects, randomizing the subjects so that the mean threshold of intensity of tinnitus was perceived at 30 dB, while the parameter of the frequency to 1-2-4-8 kHz was not considered. Group A was treated with the treatment according to the invention dispensing distilled water on nasal and paranasal mucosa at 7 g/sec for 1 sec with frequency of 1 time/day for six months, while group B was treated with frequency 10 times/day for six months. Group C was treated with the sum of therapies currently in use more (vasoactive of the microcirculation, multivitamin complex, antioxidants, ginkgo biloba).

At the end of six months, all subjects underwent a new audiometric examination and acufenometria. In group A an improvement in tinnitus was found, which was reduced to 25 dB on average in intensity; in group B, treated with a frequency ten times higher, an even greater improvement in tinnitus was detected, which dropped to 20 dB on average in intensity and disappeared in 10 patients, while in group C the tinnitus remained unchanged.

The overall results of the clinical trials described are illustrated in graphical form in FIG. 13 of the accompanying drawings, which shows the following:

Evaluation Pre-Therapy
  ⊗ Average tinnitus intensity 40 dB, in decibel hearing level (216 subjects)
Evaluation Post-Therapy
  + Group B, (72 subjects)—therapy PEL 7 g/sec, ET 1 sec, frequency 10 times/die:
  ○ Group A, (72 subjects)—therapy PEL 7 g/sec, ET 1 sec, frequency 1 time/die:
  • Group C, (72 subjects)—traditional therapies The foregoing further confirms the effectiveness of the therapy proposed, according to the invention, on nerve cells.

Experiment 10

Determination of Permissible Values of PEL, ET and Frequency of Administration

On the authors of the invention and on a group of ten family persons, the therapy has been tested to find the maximum tolerated values of PEL, ET and frequency. The tests were followed by filling out a questionnaire in which the specific issue of tolerability was addressed.

The results obtained were as follows:

PEL: values above 15 g/sec were rejected by the subjects. Treatment is tolerable in an inversely proportional manner and effective in direct proportion to the values of PEL, for values from 0.2 g/sec to 15 g/sec.

ET: values in excess of 120 sec. were rejected by the subjects. Treatment is tolerable in an inversely proportional manner and effective in a manner directly proportional to the values of ET, for values from 0.2 sec to 120 sec.

The most important results depends on the comparison between PEL and ET, who must act together and determine the effectiveness of therapy. In particular, the following operational limits have been confirmed:

therapy is effective and tolerable for values of ET from 0.2 sec to 120 sec. and PEL between 0.2 g/sec and 15 g/sec, with the proviso that each delivery does not exceed the total amount of 150 g;

therapy is tolerable in a manner inversely proportional and effective in direct proportion to the values of PEL and ET;

therapy is effective and tolerated for a frequency of administration from 1 to 10 times a day, with effectiveness and acceptability directly proportional inversely proportional to the frequency.

The present Invention has-been disclosed with reference to some specific particular embodiments thereof, but it should be understood that modifications and changes may be made by the persons skilled in the art without departing from the scope of the invention as defined in the appended claims.

The invention claimed is:

1. A method for therapy and prophylaxis of at least one pathology selected from the group consisting of pathologies of the central nervous system, pathologies of the peripheral nervous system and neurologic pathologies of the auditory, visual and olfactory apparatus, comprising selecting a water-based liquid having an osmolality not higher than 130% of a blood plasma osmolality; and stimulating endogenous production of at least one inflammatory mediator selected from the group consisting of NGF, neurotrophin-3, neurotrophin-4, serotonin, substance P, heparin, and ECF-A by administering the selected water-based liquid on a nasal-paranasal mucous membrane of the subject;

wherein the administration on the nasal-paranasal mucous membrane is carried out by dispensing an amount of the water-based liquid at a dispensing rate (PEL) ranging from 5.0 g/sec to 15 g/sec, for a dispensing time (ET) ranging from 0.4 sec to 120 sec, with the proviso that a mathematical product of ET and PEL is no greater than 150 g of the dispensed liquid in each administration;

wherein the administration on the nasal-paranasal mucous membrane is carried out at a frequency ranging from 1 to 10 times a day; and wherein said water-based liquid comprises at least one selected from the group consisting of distilled water, bidistilled water, sterile tap water, physiological solution containing NaCl from 0.9% to 0.01% by weight with optional addition of glucose, Ringer solution, Ringer lactate solution, Hartmann solution, aqueous sulphur solution with a concentration ranging from 0.1 mg to 10 mg of $H_2S$ per liter, ionized alkaline water with a pH value ranging from 8 to 11, and deionised water.

2. The method according to claim 1, wherein the administration on the nasal-paranasal mucous membrane is carried out by dispensing an amount of the selected water-based liquid at a dispensing rate (PEL) ranging from 5.0 g/sec to 15 g/sec, for a dispensing time (ET) ranging from 0.4 sec to 10 sec, with the proviso that a mathematical product of ET and PEL is no greater than 150 g of the dispensed water-based liquid in each administration.

3. The method according to claim 2, wherein the water-based liquid has an osmolality lower than or equal to a blood plasma osmolality.

4. The method according to claim 1, wherein said water-based liquid is distilled water.

5. The method according to claim 1, wherein the inflammatory mediator is NGF.

6. The method according to claim 5, wherein the pathologies are degenerative pathologies of the central nervous system or degenerative pathologies of the peripheral nervous system.

7. The method according to claim 6, wherein the pathology is at least one selected from the group consisting of Alzheimer's disease, presbiacusis, tinnitus, sudden neurosensorial hypoacusis, and progressive neurosensorial hypoacusis.

8. The method according to claim 1, wherein the inflammatory mediator is NT-3 or NT.

9. The method according to claim 1, wherein the inflammatory mediator is serotonin, and the pathologies comprise at least one selected from the group consisting of mood disturbances, restlessness, insomnia, vegetative dystonia, depression, neurasthenia, cephalalgia, eating and appetite disorders, and disorders in sleeping quality.

10. An apparatus for therapy of at least one pathology selected from the group consisting of pathologies of the central nervous system, pathologies of the peripheral nervous system and neurologic pathologies of the auditory, visual and olfactory apparatus by stimulating endogenous production of inflammatory mediators, comprising a spray dispenser configured to administer a water-based liquid on the nasal-paranasal mucous membrane of a subject, wherein the spray dispenser has a dispensing rate (PEL) ranging from 5.0 g/sec to 15 g/sec, and is configured to dispense the water-based liquid for a dispensing time (ET) ranging from 0.4 sec to 120 sec, with the proviso that a mathematical product of ET and PEL is no greater than 150 g of the dispensed water-based liquid in each administration;

wherein the water-based liquid has an osmolality not higher than 130% of a blood plasma osmolality; and wherein the inflammatory mediators are at least one inflammatory mediator selected from the group consisting of NGF, neurotrophin-3, neurotrophin-4, serotonin, substance P, heparin, and ECF-A.

11. The apparatus according to claim 10, wherein the apparatus is configured to dispense the water-based liquid comprising at least one selected from the group consisting of distilled water, bidistilled water, sterile tap water, physiological solution containing NaCl from 0.9% to 0.01% by weight with optional addition of glucose, Ringer solution, Ringer lactate solution, Hartmann solution, aqueous sulphur solution with a concentration ranging from 0.1 mg to 10 mg of $H_2S$ per liter, ionized alkaline water with a pH value ranging from 8 to 11, and deionised water.

12. The apparatus according to claim 10, wherein the dispensing rate of the spray dispenser is adjustable in the range of 5.0 g/sec to 15 g/sec, and the dispensing time (ET) is adjustable in the range of 0.4 sec to 120 sec.

13. The apparatus according to claim 10, wherein the apparatus is configured to dispense the water-based liquid to the subject at a frequency of 1 to 10 times a day.

* * * * *